US006201850B1

(12) United States Patent
Heumann

(10) Patent No.: US 6,201,850 B1
(45) Date of Patent: Mar. 13, 2001

(54) ENHANCED THICKNESS CALIBRATION AND SHADING CORRECTION FOR AUTOMATIC X-RAY INSPECTION

(75) Inventor: John M. Heumann, Loveland, CO (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/237,401

(22) Filed: Jan. 26, 1999

(51) Int. Cl.$^7$ .................................................. G01N 23/083
(52) U.S. Cl. .................................. 378/56; 378/58; 378/22
(58) Field of Search .................................. 378/22, 54, 56, 378/58

(56) References Cited

U.S. PATENT DOCUMENTS

| | | |
|---|---|---|
| Re. 35,423 | 1/1997 | Adams et al. . |
| 3,499,146 | 3/1970 | Richards . |
| 3,818,220 | 6/1974 | Richards . |
| 4,415,980 | 11/1983 | Buchanan . |
| 4,481,664 | 11/1984 | Linger et al. . |
| 4,521,902 | 6/1985 | Peugeot . |
| 4,688,241 | 8/1987 | Peugeot . |
| 4,809,308 | 2/1989 | Adams et al. . |
| 4,852,131 | 7/1989 | Armistead . |
| 4,926,452 | 5/1990 | Baker et al. . |
| 5,020,086 | 5/1991 | Peugeot . |
| 5,081,656 | 1/1992 | Baker et al. . |
| 5,097,492 | 3/1992 | Baker et al. . |
| 5,199,054 | 3/1993 | Adams et al. . |
| 5,259,012 | 11/1993 | Baker et al. . |
| 5,291,535 | 3/1994 | Baker et al. . |
| 5,319,547 * | 6/1994 | Krug et al. ........................ 364/409 |
| 5,465,152 | 11/1995 | Bilodeau et al. . |
| 5,500,886 | 3/1996 | Duff . |
| 5,561,696 * | 10/1996 | Adams et al. ........................ 378/58 |
| 5,583,904 | 12/1996 | Adams . |
| 5,592,562 | 1/1997 | Rooks . |
| 5,594,770 | 1/1997 | Bowles et al. . |
| 5,621,811 * | 4/1997 | Roder et al. ........................ 382/147 |
| 5,687,209 | 11/1997 | Adams . |

OTHER PUBLICATIONS

Hasenkamp, "Radiographic Laminography," *Materials Evaluation*, Aug. 1974, pp. 169–180.
Deane et al., IRT Corp., "Using X-Ray Vision to Verify SMD-Board Quality," *Electronics Test*, Feb. 1987, pp. 32–35.
Soron, IRT Corp., X-Ray Inspection Meets Increased PWB Throughput, Denisty Challenge–Part 1, *Electronics*, Oct. 1987, pp. 36–37.
Pound, "Image Processing Boosts the Power of Non–destructive Testing," *Electronic Packaging and Production*, Jun. 1985.

(List continued on next page.)

Primary Examiner—David V. Bruce

(57) ABSTRACT

An X-ray inspection system incorporates an improved technique for determining, in an X-ray image of a multilayered assembly, the gray level component of a first material in the presence of a second material. The total gray level of the image is dependent upon the physical characteristics of each material comprising the assembly. The present invention accurately determines the component of the total image gray level due to the first material. In the case of circuit board inspections using X-ray images of solder connections, a calibration procedure facilitates the direct conversion of the gray level component due to the solder connection to the thickness of the solder connection.

55 Claims, 13 Drawing Sheets

OTHER PUBLICATIONS

Casey, "X–Ray Inspection," *Manufacturing Systems*, Jul. 1987, p. 18ff.

Corey, IRT Corp., "Artificial Perception Gives Super Vision," *Research and Development*, Oct. 1984.

Wittenberg, "IRT Improves SMT X–Ray Inspection System," *Electronic Engineering Times*, Oct. 5, 1987, p. 53.

Phelps, Christi, "Four Pi Captures Contact, Capital; Unveils Product," *San Diego Business Journal*, Week of Oct. 10–16, 1888.

Four Pi Systems product brochure for "3DX Series 2000" Automated Inspection System, Copyright 1988.

Juha, Mike, "Automated Inspection of Surface Mounted Device Solder Connections", Proceedings of Soldering Technology Seminar–Feb. 19–20, 1985, Naval Weapons Center, China Lake, CA, Publication NWC TS 85–25, pp. 73–90.

"MV–6000 In Line SMT Process Monitor–Product Description", published by Nicolet, publication date unknown.

Kang et al., "A New X–ray Cross–Sectional Imaging System for Arbitrary Angle Inspection of BGA Package", *Proceedings of the Technical Program—NEPCON® East '97–Jun. 9–12, 1997*, Boston, Massachusetts, pp. 109–119.

\* cited by examiner

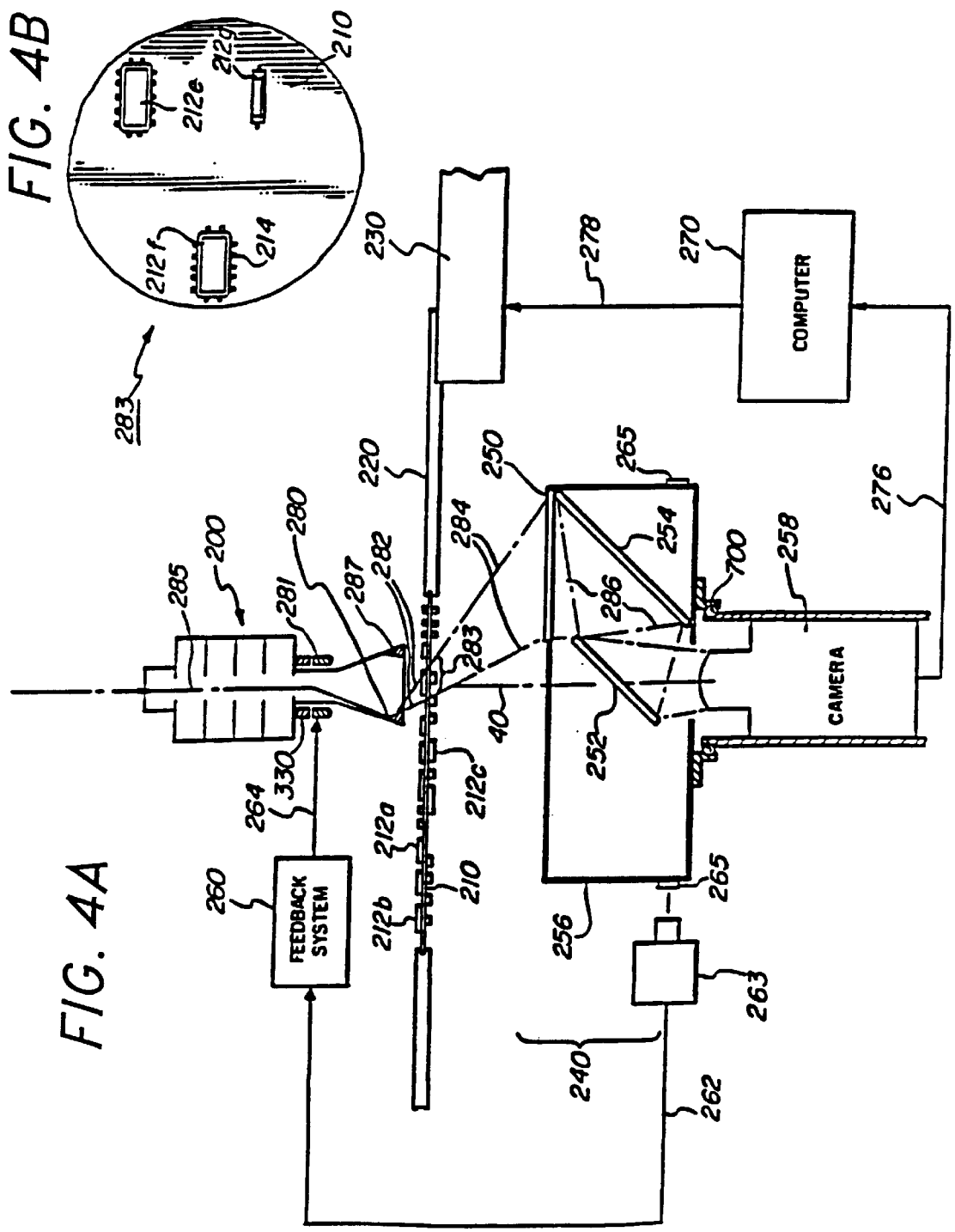

ENHANCED THICKNESS CALIBRATION AND SHADING CORRECTION FOR AUTOMATIC X-RAY INSPECTION

FIELD OF THE INVENTION

The invention relates generally to the automated X-ray inspection of printed circuit assemblies, and in particular, to systems which use X-ray images of solder joints to provide a measured thickness of the solder joint.

BACKGROUND OF THE INVENTION

Rapid and precise quality control inspections of the soldering and assembly of electronic devices have become priority items in the electronics manufacturing industry. Many existing inspection systems for electronic devices and connections make use of penetrating radiation to form images which exhibit features representative of the internal structure of the devices and connections. These systems often utilize conventional radiographic techniques wherein the penetrating radiation comprises X-rays. Medical X-ray pictures of various parts of the human body, e.g., the chest, arms, legs, spine, etc., are perhaps the most familiar examples of conventional radiographic images. The images or pictures formed represent the X-ray shadow cast by an object being inspected when it is illuminated by a beam of X-rays. The X-ray shadow is detected and recorded by an X-ray sensitive material such as film or electronic means. Alternatively, tomographic techniques such as laminography and computed tomography (CT) may be used to produce cross-sectional images of the object being inspected. Laminography systems which are capable of achieving the speed and accuracy requirements necessary for electronics inspection are described in the following patents: 1) U.S. Pat. No. 4,926,452 entitled "AUTOMATED LAMINOGRAPHY SYSTEM FOR INSPECTION OF ELECTRONICS", issued to Baker et al.; 2) U.S. Pat. No. 5,097,492 entitled "AUTOMATED LAMINOGRAPHY SYSTEM FOR INSPECTION OF ELECTRONICS", issued to Baker et al.; 3) U.S. Pat. No. 5,081,656 entitled "AUTOMATED LAMINOGRAPHY SYSTEM FOR INSPECTION OF ELECTRONICS", issued to Baker et al.; 4) U.S. Pat. No. 5,291,535 entitled "METHOD AND APPARATUS FOR DETECTING EXCESS/INSUFFICIENT SOLDER DEFECTS", issued to Baker et al.; 5) U.S. Pat. No. 5,621,811 entitled "LEARNING METHOD AND APPARATUS FOR DETECTING AND CONTROLLING SOLDER DEFECTS", issued to Roder et al.; 6) U.S. Pat. No. 5,561,696 "METHOD & APPARATUS FOR INSPECTING ELECTRICAL CONNECTIONS", issued to Adams et al.; 7) U.S. Pat. No. 5,199,054 entitled "METHOD AND APPARATUS FOR HIGH RESOLUTION INSPECTION OF ELECTRONIC ITEMS", issued to Adams et al.; 8) U.S. Pat. No. 5,259,012 entitled "LAMINOGRAPHY SYSTEM AND METHOD WITH ELECTROMAGNETICALLY DIRECTED MULTIPATH RADIATION SOURCE", issued to Baker et al.; 9) U.S. Pat. No. 5,583,904 entitled "CONTINUOUS LINEAR SCAN LAMINOGRAPHY SYSTEM AND METHOD", issued to Adams; and 10) U.S. Pat. No. 5,687,209 entitled "AUTOMATIC WARP COMPENSATION FOR LAMINOGRAPHIC CIRCUIT BOARD INSPECTION", issued to Adams. The entirety of each of the above referenced patents is hereby incorporated herein by reference.

In automated X-ray inspection (AXI) of printed circuit assemblies, gray-scale images of interconnects or slices thereof are examined to detect and classify improper joints and/or to provide statistical process control data relating to the manufacturing process. For reasons including but not limited to portability, reproducibility and clarity, it is desirable that measurements taken relate directly to physical characteristics of the joint under inspection. In characterizing solder joints, for example, it is preferable to deal with measured joint thickness rather than gray scale pixel values. However, extracting solder thickness from the measured gray scale pixel values is complicated by several factors. First, X-ray sources used in AXI typically emit X-rays at many wavelengths with varying intensities as a function of wavelength. Additionally, in passing through a printed circuit assembly, X-rays will typically encounter other absorbers in addition to the solder, e.g., copper power and ground planes, tantalum capacitors, etc. Each material has its own characteristic absorption spectrum as a function of wavelength. The resulting interaction is highly non-linear, and complete characterization of the thickness of solder and other shading materials in the path is generally not possible from a limited number of gray scale calibration measurements.

Nonetheless, useful approximations can be made when prior knowledge of the assembly under inspection is available. For example, in many cases, solder thickness may be desired and it may be known that the background shading is due almost entirely to a particular material, e.g., copper. In such cases, by measuring background (due to the copper alone) and foreground (due to both copper and solder) gray values, one may attempt to estimate solder thickness if a suitable correction for background "shading" by copper can be constructed.

Previous calibration procedures have encountered a number of difficulties in practice. For example, previous attempts which use polynomial regression techniques to fit a set of calibration points to a surface which approximates solder thickness have been deficient. Such fitted surfaces frequently have unwanted maxima, minima, saddle points and inflection points, and often do not accurately reflect the underlying physical process. Better fits may be obtained by using a more constrained surface (e.g. one which is linear along one or more axis) to a portion of the calibration surface. This helps avoid the problems that often plague higher order regression surfaces, but leads to its own difficulties. In particular, multiple "patches" are often required to approximate the entire calibration surface. In the presence of measurement noise, this can lead to inconsistent behavior for points lying near the borders of adjacent patches.

OBJECTS AND ADVANTAGES OF THE PRESENT INVENTION

It is the object of the present invention to circumvent the above described difficulties. In particular, the present invention:

a) provides a single, globally consistent calibration for any chosen material in the presence of varying amounts of shading by a second material;

b) is fast in terms of its computational requirements;

c) is compact in terms of its storage requirements;

d) is more accurate than previous methods;

e) is numerically invertible;

f) may be made traceable to known standards criteria, for example, the National Institute of Standards & Technology (NIST) or similar standards agencies. This feature permits process engineers to relate thicknesses measured by the X-ray system to physical joint dimensions. Traceability can be achieved by constructing the calibration standard out of materials of known purity, and by measuring thicknesses of the calibration standard using instruments which themselves have a traceable calibration;

g) is portable, in the sense that measurement of the same joint on multiple systems will return similar or identical thicknesses. Portability requires that the calibration compensates for the physically significant sources of variation between systems; and h) supports multiple calibrations. With the advent of lead-free solders, the joint and background compositions can vary from board to board, or even within a board. As a result, it is desirable to be able to store multiple calibrations simultaneously, and to permit the user to select the appropriate calibration on a pin, component, or board level.

SUMMARY OF THE INVENTION

The present invention comprises an improved system which provides more accurate determination of solder joint thicknesses derived from X-ray images of the solder joints. More generally, the present invention may be used to determine the quantities of two materials comprising a two component assembly. The configuration of the two materials in the assembly may be in any form, e.g., the two materials may be in two separate layers, multiple mixed layers, an homogenous mixture, etc. The two materials may themselves consist of complex chemical mixtures rather than pure elements or compounds.

Consider the special case of lead or solder shaded by copper for the purpose of simplifying the following illustration. The present invention measures the gray levels of X-ray images of a number of test coupons which contain known thicknesses of the lead or solder shaded by varying amounts of copper. By a combination of theoretical and empirical arguments, it has been found that the effect of the copper shading may be described by a particular nonlinear equation with three free parameters. Moreover, two of the three parameters are found to be characteristics of the AXI system and not functions of the amount of copper or lead/solder in the X-ray beam path. One aspect of the system calibration involves estimation and storage of these two parameters. Foreground and background gray level values from an unknown sample are adequate to fix the third parameter, completely characterizing the shading effect for that sample. As a result, it is possible to use the two stored system parameters and the known functional form of the shading equation to extrapolate to values that would have been measured under a "standard" or predetermined reference shading level. For example, "no shading", i.e., zero background, may be used as the standard condition. However, other non-zero background shading levels may also be selected as the standard condition. Since any measured sample can be readily converted to standard conditions using this approach, there is no need for a two dimensional thickness calibration. Instead, a simple one dimensional curve suffices, since measurements can always be corrected to standard conditions.

In a first aspect, the present invention includes a method for calibrating an X-ray imaging system for quantitatively determining the thickness of a first absorbing material in the presence of a second absorbing material where an incident X-ray beam having an incident X-ray beam intensity is transmitted through the first and second absorbing materials, the method comprising the steps of: providing a calibration standard having: a) multiple combinations of a first known thickness of the first absorbing material (denoted by $t_{M1,1}$) in combination with three thicknesses of the second absorbing material (denoted by $t_{M2,1}$, $t_{M2,2}$ and $t_{M2,3}$); and b) multiple combinations of a second known thickness of the first absorbing material (denoted by $t_{M1,2}$) in combination with three thicknesses of the second absorbing material (denoted by $t_{M2,4}$, $t_{M2,5}$ and $t_{M2,6}$); determining the values of first, second and third foreground parameters (denoted by $F_1$, $F_2$ and $F_3$) wherein: a) the first foreground parameter $F_1$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,1}$; b) the second foreground parameter $F_2$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,2}$; and c) the third foreground parameter $F_3$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,3}$; determining the values of first, second and third background parameters (denoted by $B_1$, $B_2$ and $B_3$) wherein: a) the first background parameter $B_1$ is representative of a transmitted X-ray beam intensity corresponding to a portion of the incident X-ray beam intensity which is transmitted through only the second absorbing material having the thickness $t_{M2,1}$; b) the second background parameter $B_2$ is representative of a transmitted X-ray beam intensity corresponding to a portion of the incident X-ray beam intensity which is transmitted through only the second absorbing material having the thickness $t_{M2,2}$; and c) the third background parameter $B_3$ is representative of a transmitted X-ray beam intensity corresponding to a portion of the incident X-ray beam intensity which is transmitted through only the second absorbing material having the thickness $t_{M2,3}$; determining the values of fourth, fifth and sixth foreground parameters (denoted by $F_4$, $F_5$ and $F_6$) wherein: a) the fourth foreground parameter $F_4$ is representative of a transmitted X-ray beam intensity corresponding to a portion of the incident X-ray beam intensity which is transmitted through the first absorbing material having the thickness $t_{M1,2}$ in combination with the second absorbing material having the thickness $t_{M2,4}$; b) the fifth foreground parameter $F_5$ is representative of a transmitted X-ray beam intensity corresponding to a portion of the incident X-ray beam intensity which is transmitted through the first absorbing material having the thickness $t_{M1,2}$ in combination with the second absorbing material having the thickness $t_{M2,5}$; and c) the sixth foreground parameter $F_6$ is representative of a transmitted X-ray beam intensity corresponding to a portion of the incident X-ray beam intensity which is transmitted through the first absorbing material having the thickness $t_{M1,2}$ in combination with the second absorbing material having the thickness $t_{M2,6}$; determining the values of fourth, fifth and sixth background parameters (denoted by $B_4$, $B_5$ and $B_6$) wherein: a) the fourth background parameter $B_4$ is representative of a transmitted X-ray beam intensity corresponding to a portion of the incident X-ray beam intensity which is transmitted through only the second absorbing material having the thickness $t_{M2,4}$; b) the fifth background parameter $B_5$ is representative of a transmitted X-ray beam intensity corresponding to a portion of the incident X-ray beam intensity which is transmitted through only the second absorbing material having the thickness $t_{M2,5}$; and c) the sixth background parameter $B_6$ is representative of a transmitted X-ray beam intensity corresponding to a portion of the incident X-ray beam intensity which is transmitted through only the second absorbing material having the thickness $t_{M2,6}$; and determining a first functional form of a non-linear function, $y_1(x)$, which describes the value of the foreground minus the background ($y_1$=F−B) as a function of background (x=B) such that the non-linear functional form: a) approximates the following values of foreground minus background: ($F_1$−$B_1$), ($F_2$−$B_2$), ($F_3$−$B_3$), ($F_4$−$B_4$), ($F_5$−$B_5$) and ($F_6$−$B_6$); b) supports extrapolation beyond the range of the values of foreground minus background {($F_1$−$B_1$), ($F_2$−$B_2$), ($F_3$−$B_3$), ($F_4$−$B_4$), ($F_5$−$B_5$), ($F_6$−$B_6$)} and/or foreground {$F_1, F_2, F_3, F_4, F_5, F_6$} and/or background {$B_1, B_2, B_3, B_4, B_5, B_6$}; and c) incorporates one or more additional constraints determined by or approximating the physical behavior of the X-ray imaging system. The steps of determining the values of the foreground and background parameters may further comprise the steps of: illuminating the calibration standard with a beam of X-rays having the incident X-ray beam intensity, wherein the beam of X-rays is produced by an X-ray source; and measuring the values of the foreground and background parameters with an X-ray detector. The steps of determining the values of the foreground and background parameters may further comprise the step of simulating the values of the foreground and background parameters using one or more of the following simulation factors: a) spectral characteristics of the X-ray source; and/or b) angular distribution of X-rays produced by the X-ray source; and/or c) stopping power and spectral sensitivity of the X-ray detector; and/or d) X-ray attenuation properties of the first and second absorbing materials as functions of X-ray energy/wavelength. The foreground parameters $F_i$ may be described by a functional form, $y_F$:

$$y_F = y_0 - \int \alpha(E) e^{-\beta(E)t_1} e^{-\gamma(E)t_2} dE$$

or its discrete approximation:

$$y_F = y_0 - \Sigma_i \alpha_i e^{-\beta_i t_1} e^{-\gamma_i t_2}$$

where $t_1$ and $t_2$ are the thicknesses of the first absorbing material and the second absorbing material, respectively; $y_0$ is a fitting constant; and, in the general functional form: a) the X-ray source energy spectrum is distributed as a function of energy with weightings determined by the parameter $\alpha(E)$; and b) $\beta(E)$ and $\gamma(E)$ are the X-ray attenuation coefficients for the first and second absorbing materials, respectively, and in the discrete approximation: c) the total X-ray source energy spectrum is split up into some number of bands i, where the total source intensity is distributed among the bands as a functions of X-ray source energy and detector sensitivity with weightings for each band i determined by the parameter $\alpha_i$; and d) $\beta_i$ and $\gamma_i$ are the effective linear attenuation coefficients for X-rays in band i for the first and second absorbing materials, respectively. The step of determining a first functional form of a smoothly varying non-linear function which expresses the value of the foreground minus the background ($y_1$=F−B) as a function of background (x=B) may also comprise the step of selecting a function of the form:

$$y_1 = \sqrt{(x-a)^2 + b^2} + c$$

where x corresponds to the background $B_i$, $y_1$ corresponds to the difference between the foreground and background ($F_i$−$B_i$), and a, b and c are fitting constants. The method may further comprise the steps of: selecting a reference background level (x=$B_R$); determining the values of foreground minus background ($F_{Ri}$−$B_{Ri}$) at the reference background level ($B_R$) for multiple known thicknesses of the calibration standard using the smoothly varying non-linear function $y_1$ which expresses the value of the foreground minus the background ($y_1$=F−B) as a function of background (x=B); and determining a second functional form $y_2$ which expresses the values of foreground minus background ($F_{Ri}$−$B_{Ri}$) at the reference background level ($B_R$) for the multiple known thicknesses of the first absorbing material as a function of the thickness of the first absorbing material. The step of determining a second functional form $y_2$ may further comprise the step of selecting a function which is a sum of exponentials of the form:

$$y_2(t) = p - \Sigma_i q_i e^{-r_i t}$$

where p, $q_i$ and $r_i$ are fitting constants. The method may further include the step of producing a lookup table for values of (background) vs. (foreground minus background) vs. (thickness) for one or both of the first and/or second absorbing materials. The method may also further comprise the steps of: determining the value of a seventh foreground parameter (denoted by $F_7$) which is representative of a transmitted X-ray beam intensity corresponding to a portion of the incident X-ray beam intensity which is transmitted through the first absorbing material having an unknown thickness $t_{M1,7}$ in combination with the second absorbing material having an unknown thickness $t_{M2,7}$; determining the value of a seventh background parameter (denoted by $B_7$) which is representative of a transmitted X-ray beam intensity corresponding to a portion of the incident X-ray beam intensity which is transmitted through the second absorbing material having an unknown thickness $t_{M2,7}$; and using the lookup table and the values of $F_7$ and $B_7$ to determine one or both of the unknown thickness(es) of the first absorbing material ($t_{M1,7}$) and/or the second absorbing material ($t_{M2,7}$). This method may also include the step of interpolating between values in the lookup table. The step of interpolating may further comprise the step of bilinear interpolation. The method may further include the step of selecting the thicknesses of the second absorbing material ($t_{M2,i}$) such that at least one of the values of the first, second and third background parameters (denoted by $B_1$, $B_2$ and $B_3$) is equal to at least one of the values of the fourth, fifth and sixth background parameters (denoted by $B_4$, $B_5$ and $B_6$). Similarly, the method may further comprise the step of selecting the thicknesses of the second absorbing material ($t_{M2,i}$) such that at least two of the values of the first, second and third background parameters (denoted by $B_1$, $B_2$ and $B_3$) are equal and/or at least two of the values of the fourth, fifth and sixth background parameters (denoted by $B_4$, $B_5$ and $B_6$) are equal.

In a second aspect, the present invention includes a method for measuring the thickness of a first material in the presence of a second material comprising the steps of: providing a calibration standard having: a) multiple combinations of a first known thickness of the first material in combination with a range of thicknesses of the second material; and b) multiple combinations of a second known thickness of the first material in combination with a range of thicknesses of the second material; exposing the calibration standard to a source of transmissive energy having an incident intensity; detecting the intensity of the transmissive energy which passes through the calibration standard, the detecting step further comprising the step of: acquiring multiple pairs of image data which are representative of a portion of the transmissive energy which is measured after transmission through the first and second materials, where a foreground value (F) in each pair of image data corresponds to a portion of the incident intensity which is transmitted through the known thickness of the first material in combination with one of the multiple thicknesses of the second material, and a background value (B) in each pair of transmitted intensities corresponds to a portion of the incident intensity which is transmitted through only the corresponding thickness of the second material which was in combination with the first material when the foreground value (F) was acquired; determining fitting constants a,b and c for each member of a family of hyperbolic curves which describe delta gray values ($y_1=\Delta G=F-B$) as a function of background values (B), where each curve in the family represents delta gray values for a fixed known thickness of the first material in combination with a range of thicknesses of the second material, each of the hyperbolic curves having the general form of:

$$y_1=\sqrt{(x-a)^2+b^2}+c$$

where x corresponds to the background values (x=B); $y_1$ corresponds to the delta gray values ($y_1=\Delta G=F-B$) for a fixed known thickness of the first material in combination with the range of thicknesses of the second material; and a, b and c are the fitting constants, wherein the fitting constants are determined such that each hyperbolic curve in the family has the same x-axis intercept ($BG_{MAX}$,0) and each hyperbolic curve in the family has a minimum value at the same value of x (x=a); determining for each known thickness of the first material, a delta gray level at a reference background level, i.e., $y_1(x=B_R)$, from the hyperbolic curve defined by the multiple pairs of image data for the respective known thickness of the first material; and determining fitting constants for a second functional form ($y_2$) which describes the delta gray level values at the reference background level, as a function of the known thicknesses (t) of the first material, where the functional form is:

$$y_2(t)=BG_{MAX}-\beta e^{-k_1 t}-(BG_{MAX}-\beta)e^{-k_2 t}$$

where fitting constants $\beta$, $k_1$ and $k_2$ are determined by fits to the known thicknesses of the first material and corresponding delta gray levels at the reference background level derived from the hyperbolic curves which describe the delta gray values ($y_1$) as a function of the background values (B).

A third aspect of the present invention is method for measuring the thickness of a first material in the presence of a second material comprising the steps of: providing a calibration standard having: a) multiple combinations of a first known thickness ($t_{M1,1}$) of the first material in combination with a range of thicknesses ($t_{M2,a}$, $t_{M2,b}$, ..., $t_{M2,n1}$) of the second material; and b) multiple combinations of a second known thickness ($t_{M1,2}$) of the first material in combination with a range of thicknesses ($t_{M2,n1+1}$, $t_{M2,n1+2}$, ..., $t_{M2,n1+n2}$) of the second material; exposing the calibration standard to a source of transmissive energy having an incident intensity; detecting the intensity of the transmissive energy which passes through the calibration standard and determining therefrom image data which are representative of a portion of the transmissive energy which is measured after transmission through the first and second materials, the detecting step further comprising the step of: acquiring multiple pairs of image data, where each pair includes a foreground value and a background value, for each known thickness of the first material ($t_{M1,1}$, $t_{M1,2}$) in combination with multiple thicknesses ($t_{M2,a}$, $t_{M2,b}$, etc.) of the second material; where the foreground value ($y_f$) in each pair of image data corresponds to a portion of the incident intensity which is measured after transmission through the known thickness of the first material in combination with one of the multiple thicknesses of the second material, and the background value ($y_b$) in each pair of image data corresponds to a portion of the incident intensity which is measured after transmission through the corresponding thickness of the second material which was in combination with the first material when the foreground value ($y_F$) was acquired; determining fitting constants $y_0$, $\alpha_i$ and $\beta_i$ from the calibration standard background values for a functional form which approximates the measured background values ($y_b$) as a function of the thickness, wherein the functional form is:

$$y_b=y_0-\Sigma_i \alpha_i e^{-\beta_i t_{M2}}$$

determining fitting constants $y_i$, using the previously determined fitting constants $y_0$, $\alpha_i$ and $\beta_i$ from the calibration standard background values, for a functional form which approximates the measured foreground values ($y_f$) as a function of the thickness, wherein the functional form is:

$$y_f=y_0-\Sigma_i \alpha_i e^{-\beta_i t_{M2}} e^{-\gamma_i t_{M1}}$$

where $t_{M1}$ and $t_{M2}$ are the thicknesses of the first material and the second material, respectively; and generating a Background ($y_b$) vs. Delta Gray ($\Delta G=y_f-y_b$) vs. First Material Thickness ($t_{M1}$) surface using the fitted values for $y_0$, $\alpha_i, \gamma_i$ and $\beta_i$. The step of acquiring multiple pairs of image data may include the step of simulating the intensities of the transmissive energy which passes through the calibration standard using one or more of the following simulation factors: a) spectral characteristics of the source of transmissive energy; and/or b) angular distribution of the source of transmissive energy; and/or c) stopping power and spectral sensitivity of a transmissive energy detector; and/or d) transmissive energy attenuation properties of the absorbing material as a function of energy/wavelength of the source of transmissive energy. This method may further comprise the steps of: measuring foreground and background values for a combination of the first and second materials having unknown thicknesses; and locating on the Background ($y_b$) vs. Delta Gray ($\Delta G=y_f-y_b$) vs. First Material Thickness ($t_{M1}$) surface, background and Delta Gray image data values corresponding to the measured background and foreground values to determine at least one of the corresponding first and/or second material thicknesses. This method may further comprise the step of generating a Background ($y_b$) vs. Delta Gray ($\Delta G=y_f-y_b$) vs. First Material Thickness ($t_{M1}$) and/or Second Material Thickness ($t_{M2}$) look up table using the fitted values for $y_0$, $\alpha_i, \gamma_i$ and $\beta_i$. Additionally, the method may also comprise the steps of: measuring foreground and background values for a combination of the first and second materials having unknown thicknesses; and locating on the Background ($y_b$) vs. Delta Gray ($\Delta G=y_f-y_b$) vs. First Material Thickness ($t_{M1}$) look up table, Background and Delta Gray intensity values corresponding to the measured background and foreground values to determine at least one of the corresponding first and/or second material thicknesses. The method may also include the step of interpolating between values in the lookup table.

In a fourth aspect, the invention is a method for calibrating an X-ray imaging system for quantitatively determining the thickness of a first absorbing material in the presence of a second absorbing material where an incident X-ray beam having an incident X-ray beam intensity is transmitted through the first and second absorbing materials, the method comprising the steps of: providing a calibration standard for characterizing the imaging system wherein the calibration standard includes a first known thickness of the first absorbing material (denoted by $t_{M1,1}$) in combination with two different thicknesses of the second absorbing material (denoted by $t_{M2,1}$ and $t_{M2,2}$); determining values of first and second foreground parameters (denoted by $F_1$ and $F_2$) wherein: a) the first foreground parameter $F_1$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,1}$; and b) the second foreground parameter $F_2$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,2}$; determining values of first and second background parameters (denoted by $B_1$ and $B_2$) wherein: a) the first background parameter $B_1$ is representative of a transmitted X-ray beam intensity corresponding to a portion of the incident X-ray beam intensity which is transmitted through only the second absorbing material having the thickness $t_{M2,1}$; and b) the second background parameter $B_2$ is representative of a transmitted X-ray beam intensity corresponding to a portion of the incident X-ray beam intensity which is transmitted through only the second absorbing material having the thickness $t_{M2,2}$; determining a first non-linear functional form, $y_1(x)$, which describes values of foreground ($y_1=F$) as functions of the background ($x=B$) such that the first non-linear functional form: a) approximates the previously determined values of the first and second foreground parameters ($F_1$ and $F_2$) in terms of the previously determined values of the first and second background parameters ($B_1$ and $B_2$); b) incorporates one or more additional constraints determined by or approximating the physical behavior of the X-ray imaging system; and c) provides means to extrapolate a third foreground parameter ($F_3$) at a corresponding third background parameter ($B_3$) to a reference background value ($x=B_R$), thereby determining a reference foreground value ($y_1=F_R$) at the reference background value ($x=B_R$); and determining a second non-linear functional form, $y_2(x)$, which describes reference foreground values ($y_2=F_{Ri}$) as a function of corresponding first absorbing material thicknesses ($x=t_{M1,i}$) such that the second non-linear functional form: a) approximates a reference foreground value ($y_2=F_{R1}$) of the calibration standard first known thickness of the first absorbing material ($t_{M1,1}$) at the reference background value ($x=B_R$); and b) incorporates one or more additional constraints determined by or approximating the physical behavior of the X-ray imaging system. The step of determining a first non-linear functional form, $y_1(x)$, may further comprise the step of selecting hyperbolic functions as one of the additional constraints having characteristics determined by or approximating the physical behavior of the X-ray imaging system. The step of determining a second non-linear functional form, $y_2(x)$, may further comprise the step of inverting, either numerically or analytically, the second non-linear functional form to obtain a first material thickness ($t_{M1,K}$) corresponding to a given reference foreground value ($y_2=F_{RK}$). The step of determining a second non-linear functional form, $y_2(x)$, may further comprise the step of selecting a sum of exponential functions as one of the additional constraints having characteristics determined by or approximating the physical behavior of the X-ray imaging system. In this method, the steps of determining the values of the foreground and background parameters may further comprise the step of simulating the values of the foreground and background parameters using one or more of the following simulation factors: a) spectral characteristics of an X-ray source; and/or b) angular distribution of X-rays produced by the X-ray source; and/or c) stopping power and spectral sensitivity of an X-ray detector; and/or d) X-ray attenuation properties of the first and second absorbing materials as functions of X-ray energy/wavelength.

A fifth aspect of the present invention is a method for calibrating an X-ray imaging system for quantitatively determining the thickness of a first absorbing material in the presence of a second absorbing material where an incident X-ray beam having an incident X-ray beam intensity is transmitted through the first and second absorbing materials, the method comprising the steps of: providing a calibration standard for characterizing the imaging system wherein the calibration standard includes a first known thickness of the first absorbing material (denoted by $t_{M1,1}$) in combination with two different thicknesses of the second absorbing material (denoted by $t_{M2,1}$ and $t_{M2,2}$); determining values of first and second foreground parameters (denoted by $F_1$ and $F_2$) wherein: a) the first foreground parameter $F_1$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,1}$; and b) the second foreground parameter $F_2$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,2}$; determining values of first and second background parameters (denoted by $B_1$ and $B_2$) wherein: a) the first background parameter $B_1$ is representative of a transmitted X-ray beam intensity corresponding to a portion of the incident X-ray beam intensity which is transmitted through only the second absorbing material having the thickness $t_{M2,1}$; and b) the second background parameter $B_2$ is representative of a transmitted X-ray beam intensity corresponding to a portion of the incident X-ray beam intensity which is transmitted through only the second absorbing material having the thickness $t_{M2,2}$; and determining a functional form of a non-linear function, $y(x_1,x_2)$, which describes the value of the thickness of the first material ($y=t_{M1}$) as a function of the foreground and background (e.g., $x_1=F$, $x_2=B$) such that the non-linear functional form: a) approximates a set of calibration data points $\{(t_{M1,i},F_i,B_i)\}$ containing the previously determined first material thicknesses ($t_{M1,i}$), foreground parameters ($F_i$) and background parameters ($B_i$); b) incorporates one or more additional constraints determined by or approximating the physical behavior of the X-ray imaging system; and c) provides means to extrapolate beyond the range of the calibration standard foreground and background parameters. The step of determining a functional form of the non-linear function, $y(x_1,x_2)$, may further comprise the step of selecting a sum of the product of two exponentials to represent the foreground parameters and a sum of single exponentials to represent the background parameters as the additional constraints having characteristics determined by or approximating the physical behavior of the X-ray imaging system. The step of determining a functional form of the non-linear function, $y(x_1,x_2)$, may further comprise the step of inverting, either numerically or analytically, the non-linear functional form such that any one of y, $x_1$ or $x_2$ may be expressed as a function of the remaining two variables. In this method, the steps of determining the values of the foreground and background parameters may further comprise the step of simulating the values of the foreground and background parameters using one or more of the following simulation factors: a) spectral characteristics of an X-ray source; and/or b) angular distribution of X-rays produced by the X-ray source; and/or c) stopping power and spectral sensitivity of an X-ray detector; and/or d) X-ray attenuation properties of the first and second absorbing materials as functions of X-ray energy/wavelength.

In a sixth aspect, the present invention is a method for calibrating an X-ray imaging system for quantitatively determining the thickness of a first absorbing material in the presence of a second absorbing material where an incident X-ray beam having an incident X-ray beam intensity is transmitted through the first and second absorbing materials, the method comprising the steps of: providing a calibration standard for characterizing the imaging system wherein the calibration standard includes first and second known thicknesses of the first absorbing material (denoted by $t_{M1,1}$ and $t_{M1,2}$) in combination with a thickness of the second absorbing material (denoted by $t_{M2,1}$ and $t_{M2,2}$); determining values of first and second foreground parameters (denoted by $F_1$ and $F_2$) wherein: a) the first foreground parameter $F_1$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,1}$; and b) the second foreground parameter $F_2$ is representative of a transmitted X-ray beam intensity corresponding to a portion of the incident X-ray beam intensity which is transmitted through the first absorbing material having the thickness $t_{M1,2}$ in combination with the second absorbing material having the thickness $t_{M2,2}$; determining values of first and second background parameters (denoted by $B_1$ and $B_2$) wherein: a) the first background parameter $B_1$ is representative of a transmitted X-ray beam intensity corresponding to a portion of the incident X-ray beam intensity which is transmitted through only the second absorbing material having the thickness $t_{M2,1}$; and b) the second background parameter $B_2$ is representative of a transmitted X-ray beam intensity corresponding to a portion of the incident X-ray beam intensity which is transmitted through only the second absorbing material having the thickness $t_{M2,2}$; determining a first non-linear functional form, $y_1(x)$, which describes values of foreground ($y_1=F$) as functions of the background ($x=B$) such that the first non-linear functional form: a) approximates the previously determined values of the first and second foreground parameters ($F_1$ and $F_2$) in terms of the previously determined values of the first and second background parameters ($B_1$ and $B_2$); b) incorporates one or more additional constraints determined by or approximating the physical behavior of the X-ray imaging system; and c) provides means to extrapolate a third foreground parameter ($F_3$) at a corresponding third background parameter ($B_3$) to a reference background value ($x=B_R$), thereby determining a reference foreground value ($y^1=F_R$) at the reference background value ($x=B_R$); and determining a second non-linear functional form, $y_2(x)$, which describes reference foreground values ($y_2=F_{Ri}$) as a function of corresponding first absorbing material thicknesses ($x=t_{M1,i}$) such that the second non-linear functional form: a) approximates a first reference foreground value ($y_2=F_{R1}$) of the calibration standard first known thickness of the first absorbing material ($t_{M1,1}$) at the reference background value ($x=B_R$) and a second reference foreground value ($y^2=F_{R2}$) of the calibration standard second known thickness of the first absorbing material ($t_{M1,2}$) at the reference background value ($x=B_R$); and b) incorporates one or more additional constraints determined by or approximating the physical behavior of the X-ray imaging system. The step of providing a calibration standard may further include the step of selecting the second absorbing material such that the thickness $t_{M2,1}$ equals the thickness $t_{M2,2}$. The step of determining a first non-linear functional form, $y_1(x)$, may further comprise the step of selecting hyperbolic functions as one of the additional constraints having characteristics determined by or approximating the physical behavior of the X-ray imaging system. In this method, the step of determining a second non-linear functional form, $y_2(x)$, may further comprise the step of inverting, either numerically or analytically, the second non-linear functional form to obtain a first material thickness ($t_{M1,K}$) corresponding to a given reference foreground value ($y_2=F_{RK}$). The step of determining a second non-linear functional form, $y_2(x)$, may further comprise the step of selecting a sum of exponential functions as one of the additional constraints having characteristics determined by or approximating the physical behavior of the X-ray imaging system. Additionally, the steps of determining the values of the foreground and background parameters may further comprise the step of simulating the values of the foreground and background parameters using one or more of the following simulation factors: a) spectral characteristics of an X-ray source; and/or b) angular distribution of X-rays produced by the X-ray source; and/or c) stopping power and spectral sensitivity of an X-ray detector; and/or d) X-ray attenuation properties of the first and second absorbing materials as functions of X-ray energy/wavelength.

In a seventh aspect, the present invention is a method for calibrating an X-ray imaging system for quantitatively determining the thickness of a first absorbing material in the presence of a second absorbing material where an incident X-ray beam having an incident X-ray beam intensity is transmitted through the first and second absorbing materials, the method comprising the steps of: providing a calibration standard for characterizing the imaging system wherein the calibration standard includes first and second known thicknesses of the first absorbing material (denoted by $t_{M1,1}$ and $t_{M1,2}$) in combination with a thickness of the second absorbing material (denoted by $t_{M2,1}$ and $t_{M2,2}$); determining values of first and second foreground parameters (denoted by $F_1$ and $F_2$) wherein: a) the first foreground parameter $F_1$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,1}$; and b) the second foreground parameter $F_2$ is representative of a transmitted X-ray beam intensity corresponding to a portion of the incident X-ray beam intensity which is transmitted through the first absorbing material having the thickness $t_{M1,2}$ in combination with the second absorbing material having the thickness $t_{M2,2}$; determining values of first and second background parameters (denoted by $B_1$ and $B_2$) wherein: a) the first background parameter $B_1$ is representative of a transmitted X-ray beam intensity corresponding to a portion of the incident X-ray beam intensity which is transmitted through only the second absorbing material having the thickness $t_{M2,1}$; and b) the second background parameter $B_2$ is representative of a transmitted X-ray beam intensity corresponding to a portion of the incident X-ray beam intensity which is transmitted through only the second absorbing material having the thickness $t_{M2,2}$; and determining a functional form of a non-linear function, $y(x_1,x_2)$, which describes the values of the thickness of the first material ($y=t_{M1}$) as a function of the foreground and background (e.g., $x_1=F$, $x_2=B$) such that the non-linear functional form: a) approximates a set of calibration data points $\{(t_{M1,i}, F_i, B_i)\}$ containing the previously determined first material thicknesses ($t_{M1,i}$), foreground parameters ($F_i$) and background parameters ($B_i$); b) incorporates one or more additional constraints determined by or approximating the physical behavior of the X-ray imaging system; and c) provides means to extrapolate beyond the range of the calibration standard foreground and background parameters. The step of providing a calibration standard may further comprise the step of selecting the second absorbing material such that the thickness $t_{M2,1}$ equals the thickness $t_{M2,2}$. In this method, the step of determining a functional form of the non-linear function, $y(x_1,x_2)$, may further comprise the step of selecting a sum of the product of two exponentials to represent the foreground parameters and a sum of single exponentials to represent the background parameters as the additional constraints having characteristics determined by or approximating the physical behavior of the X-ray imaging system. The step of determining a functional form of the non-linear function, $y(x_1,x_2)$, may further comprise the step of inverting, either numerically or analytically, the non-linear functional form such that any one of y, $x_1$ or $x_2$ may be expressed as a function of the remaining two variables. Additionally, the steps of determining the values of the foreground and background parameters may further comprise the step of simulating the values of the foreground and background parameters using one or more of the following simulation factors: a) spectral characteristics of an X-ray source; and/or b) angular distribution of X-rays produced by the X-ray source; and/or c) stopping power and spectral sensitivity of an X-ray detector; and/or d) X-ray attenuation properties of the first and second absorbing materials as functions of X-ray energy/wavelength.

An eighth aspect of the present invention is a method for calibrating an X-ray imaging system for quantitatively determining a first thickness, $T_x$, of an absorbing material in the presence of an additional, second thickness, $T_y$, of the absorbing material, where an incident X-ray beam having an incident X-ray beam intensity is transmitted through the absorbing material, the method comprising the steps of: providing a calibration standard for characterizing the imaging system wherein the calibration standard provides two known thicknesses $T_1$ and $T_2$ of the absorbing material; determining values $F_1$ and $F_2$ reflective of transmitted X-ray beam intensities corresponding to transmission through thicknesses $T_1$ and $T_2$ of the absorbing material, respectively; determining a functional form of an invertible, non-linear function $y(x)$ which describes the variation of transmitted X-ray beam intensity as a function of thickness of the absorbing material; determining values B and F reflective of transmitted X-ray beam intensities corresponding to transmission through the second thickness, $T_y$, of the absorbing material and through the combined thickness, $T_x+T_y$, of the absorbing material, respectively; applying the previously determined functional form to determine $T_y$ and $T_x+T_y$ from the measured values of F and B; and determining the unknown first thickness, $T_x$, as the difference $(T_x+T_y)-T_y$. The step of determining a functional form which describes transmitted beam intensity as a function of thickness may further comprise selecting a general functional form described by:

$$y=y_0-\int \alpha(E)e^{-\beta(E)T}dE$$

or its discrete approximation:

$$y=y_0-\Sigma_i \alpha_i e^{-\beta_i T}$$

where T is the thickness of the absorbing material, $y_0$ is a fitting constant; and, in the general functional form: a) the X-ray source energy spectrum is distributed as a function of energy with weightings determined by the parameter $\alpha(E)$; and b) $\beta(E)$ is the X-ray attenuation coefficient for the absorbing material, and in the discrete approximation: c) the total X-ray source energy spectrum is split up into some number of bands i, where the total source intensity is distributed among the bands as a functions of X-ray source energy and detector sensitivity with weightings for each band i determined by the parameter $\alpha_i$; and d) $\beta_i$ is the effective linear attenuation coefficient for X-rays in band i for the absorbing material. The step of determining the values $F_1$ and $F_2$ may comprise the step of simulating the transmitted intensities using one or more of the following simulation factors: a) spectral characteristics of the incident X-ray beam; and/or b) angular distribution of X-rays comprising the incident X-ray beam; and/or c) stopping power and spectral sensitivity of an X-ray detector; and/or d) X-ray attenuation properties of the absorbing material as a function of X-ray energy/wavelength.

A ninth aspect of the present invention is an apparatus for calibrating an X-ray imaging system for quantitatively determining the thickness of a first absorbing material in the presence of a second absorbing material where an incident X-ray beam having an incident X-ray beam intensity is transmitted through the first and second absorbing materials, the apparatus comprising: a calibration standard for characterizing the imaging system wherein the calibration standard includes at least one known thickness $t_{M1,i}$ of the first absorbing material in combination with at least one thickness $t_{M2,i}$ of the second absorbing material; means for determining a value of foreground and background parameters (denoted by F and B) wherein: a) the foreground parameter F is representative of a transmitted X-ray beam intensity corresponding to a portion of the incident X-ray beam intensity which is transmitted through the first absorbing material having thickness $t_{M1,i}$ in combination with the second absorbing material having a thickness $t_{M2,i}$; and b) the background parameter B is representative of a transmitted X-ray beam intensity corresponding to a portion of the incident X-ray beam intensity which is transmitted through only the second absorbing material having the thickness $t_{M2,i}$; and means for determining a non-linear functional form which describes values of the foreground and/or the background and/or the material thicknesses such that the non-linear functional form: a) is consistent with the previously determined foreground parameter (F), background parameter (B), and thickness values; b) incorporates one or more additional constraints determined by or approximating the physical behavior of the X-ray imaging system; and c) provides means to extrapolate the foreground and/or the background and/or the material thicknesses beyond the range of the calibration standard. The means for determining a non-linear functional form may further include: means for determining a first non-linear functional form, $y_1(x)$, which describes values of foreground ($y_1=F$) as functions of the background (x=B) such that the first non-linear functional form: a) approximates the previously determined value of the foreground parameter (F) in terms of the previously determined value of the background parameter (B); b) incorporates one or more additional constraints determined by or approximating the physical behavior of the X-ray imaging system; and c) provides means to extrapolate a measured foreground parameter ($F_M$) corresponding to a first absorbing material having an unknown thickness $t_{M1,U}$ in combination with a second absorbing material having a thickness $t_{M2,U}$ to a reference background value ($x=B_R$), thereby determining a reference foreground value ($y_1=F_{R,U}$) at the reference background value ($x=B_R$); and means for determining a second non-linear functional form, $y_2(x)$, which describes reference foreground values ($y^2=F_{Ri}$) as a function of corresponding first absorbing material thicknesses ($x=t_{M1,i}$) such that the second non-linear functional form: a) approximates a reference foreground value ($y^2=F_{R1}$) of the calibration standard for the known thickness of the first absorbing material ($t_{M1,1}$) at the reference background value ($x=B_R$); and b) incorporates one or more additional constraints determined by or approximating the physical behavior of the X-ray imaging system. The means for determining a non-linear functional form may further comprise: means for determining a functional form of a non-linear function, $y(x_1,x_2)$, which describes the values of the thickness of the first material ($y=t_{M1}$) as a function of the foreground and background (e.g., $x_1=F$, $x_2=B$) such that the non-linear functional form: a) approximates a set of calibration data points $\{(t_{M1,i},F_i,B_i)\}$ containing the previously determined first material thicknesses ($t_{M1,i}$), foreground parameters ($F_i$) and background parameters ($B_i$); b) incorporates one or more additional constraints determined by or approximating the physical behavior of the X-ray imaging system; and c) provides means to extrapolate beyond the range of the calibration standard foreground and background parameters.

A tenth aspect of the present invention is a method for calibrating an X-ray imaging system for quantitatively determining the thickness of a first absorbing material in the presence of a second absorbing material where an incident X-ray beam having an incident X-ray beam intensity is transmitted through the first and second absorbing materials, the method comprising the steps of: providing a calibration standard for characterizing the imaging system wherein the calibration standard includes at least one known thickness $t_{M1,i}$ of the first absorbing material in combination with at least one thickness $t_{M2,i}$ of the second absorbing material; determining a value of foreground and background parameters (denoted by F and B) wherein: a) the foreground parameter F is representative of a transmitted X-ray beam intensity corresponding to a portion of the incident X-ray beam intensity which is transmitted through the first absorbing material having thickness $t_{M1,i}$ in combination with the second absorbing material having a thickness $t_{M2,i}$; and b) the background parameter B is representative of a transmitted X-ray beam intensity corresponding to a portion of the incident X-ray beam intensity which is transmitted through only the second absorbing material having the thickness $t_{M2,i}$; and determining a non-linear functional form which describes values of the foreground and/or the background and/or the material thicknesses such that the non-linear functional form: a) is consistent with the previously determined foreground parameter (F), background parameter (B), and thickness values; b) incorporates one or more additional constraints determined by or approximating the physical behavior of the X-ray imaging system; and c) provides means to extrapolate the foreground and/or the background and/or the material thicknesses beyond the range of the calibration standard. The step of determining a non-linear functional form may further include the steps of: determining a first non-linear functional form, $y_1(x)$, which describes values of foreground ($y_1=F$) as functions of the background ($x=B$) such that the first non-linear functional form: a) approximates the previously determined value of the foreground parameter (F) in terms of the previously determined value of the background parameter (B); b) incorporates one or more additional constraints determined by or approximating the physical behavior of the X-ray imaging system; and c) provides means to extrapolate a measured foreground parameter ($F_M$) corresponding to a first absorbing material having an unknown thickness $t_{M1,U}$ in combination with a second absorbing material having a thickness $t_{M2,U}$ to a reference background value ($x=B_R$), thereby determining a reference foreground value ($y_1=F_{R,U}$) at the reference background value ($x=B_R$); and determining a second non-linear functional form, $y_2(x)$, which describes reference foreground values ($y_2=F_{Ri}$) as a function of corresponding first absorbing material thicknesses ($x=t_{M1,i}$) such that the second non-linear functional form: a) approximates a reference foreground value ($y^2=F_{R1}$) of the calibration standard for the known thickness of the first absorbing material ($t_{M1,1}$) at the reference background value ($x=B_R$); and b) incorporates one or more additional constraints determined by or approximating the physical behavior of the X-ray imaging system. The steps of determining the values of the foreground and background parameters may further comprise the step of simulating the values of the foreground and background parameters using one or more of the following simulation factors: a) spectral characteristics of the X-ray beam; and/or b) angular distribution of X-rays comprising the X-ray beam; and/or c) stopping power and spectral sensitivity of an X-ray detector; and/or d) X-ray attenuation properties of the first and second absorbing materials as functions of X-ray energy/wavelength. In this method, the foreground parameters $F_i$ may be described by a general functional form, $y_F$:

$$y_F = y_0 - \int \alpha(E) e^{-\beta(E)t_1} e^{-\gamma(E)t_2} dE$$

or its discrete approximation:

$$y_F = y_0 - \Sigma_i \alpha_i e^{-\beta_i t_1} e^{-\gamma_i t_2}$$

where $t_1$ and $t_2$ are the thicknesses of the first absorbing material and the second absorbing material, respectively; $y_0$ is a fitting constant; and, in the general functional form: a) the X-ray beam energy spectrum is distributed as a function of energy with weightings determined by the parameter $\alpha(E)$; and b) $\beta(E)$ and $\gamma(E)$ are the X-ray attenuation coefficients for the first and second absorbing materials, respectively, and in the discrete approximation: c) the total X-ray beam energy spectrum is split up into some number of bands i, where the total source intensity is distributed among the bands as a functions of X-ray beam energy and detector sensitivity with weightings for each band i determined by the parameter $\alpha_i$; and d) $\beta_i$ and $\gamma_{i1}$ are the effective linear attenuation coefficients for X-rays in band i for the first and second absorbing materials, respectively. The step of determining a non-linear functional form may further comprise the step of selecting a function of the form:

$$y_1 = \sqrt{(x-a)^2 + b^2} + c$$

where x corresponds to the background B, $y_1$ corresponds to the difference between the foreground and background (F−B), and a, b and c are fitting constants. The method may further comprise the steps of: selecting a reference background level ($x=B_R$); determining the values of foreground minus background ($F_{Ri}-B_{Ri}$) at the reference background level ($B_R$) for multiple known thicknesses of the calibration standard using the smoothly varying non-linear function $y_1$ which expresses the value of the foreground minus the background ($y_1=F-B$) as a function of background ($x=B$); and determining a second functional form $y_2$ which expresses the values of foreground minus background ($F_{Ri}-$ $B_{Ri}$) at the reference background level ($B_R$) for the multiple known thicknesses of the first absorbing material as a function of the thickness of the first absorbing material. The step of determining a second functional form $y_2$ may further comprise the step of selecting a function which is a sum of exponentials of the form:

$$y_2(t)=p-\Sigma_i q_i e^{-r_i t}$$

where p, $q_i$ and $r_i$ are fitting constants. This method may further comprise the step of producing a lookup table for values of (background) vs. (foreground minus background) vs. (thickness) for one or both of the first and/or second absorbing materials. The step of determining a non-linear functional form may further comprise the step of: determining a functional form of a non-linear function, $y(x_1,x_2)$, which describes the values of the thickness of the first material ($y=t_{M1}$) as a function of the foreground and background (e.g., $x_1=F$, $x_2=B$) such that the non-linear functional form: a) approximates a set of calibration data points $\{(t_{M1,i}, F_i, B_i)\}$ containing the previously determined first material thicknesses ($t_{M1,i}$), foreground parameters ($F_i$) and background parameters ($B_i$); b) incorporates one or more additional constraints determined by or approximating the physical behavior of the X-ray imaging system; and c) provides means to extrapolate beyond the range of the calibration standard foreground and background parameters.

These and other characteristics of the present invention will become apparent through reference to the following detailed description of the preferred embodiments and accompanying drawings.

BRIEF DESCRIPTION OF THE DRAWINGS

FIG. 4A is a diagrammatic cross-sectional view of a circuit board inspection laminography system showing how the laminographic image is formed and viewed by a camera.

FIG. 4B shows a top view enlargement of an inspection region shown in FIG. 4A.

Figure 1A:
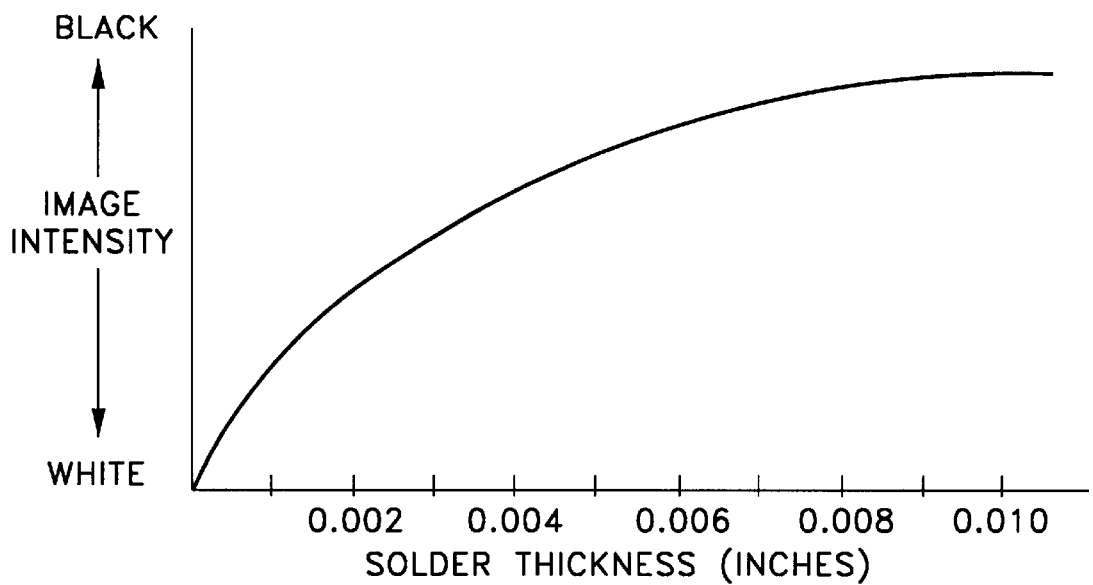
FIG. 1A is a graphical representation of the gray scale image intensity versus solder thickness for an X-ray image of solder material.

| Reference Numerals in Drawings |
| --- |
| 4 step wedge |
| 8 step wedge steps |
| 8' step wedge image intensities |
| 10 object under inspection |
| 20 source of X-rays |
| 30 X-ray detector |
| 40 common axis of rotation |
| 50 central ray |
| 60 image plane in object 10 |
| 60a arrow image plane |
| 60b circle image plane |
| 60c cross image plane |
| 62 plane of source of X-rays |
| 64 plane of X-ray detector |
| 70 point of intersection |
| 81 arrow test pattern |
| 82 circle test pattern |
| 83 cross test pattern |
| 100 image of arrow 81 |
| 102 blurred region |
| 110 image of circle 82 |
| 112 blurred region |
| 120 image of cross 83 |
| 122 blurred region |
| 130 image of arrow 81 |
| 132 image of circle 82 |
| 134 image of cross 83 |
| 200 X-ray tube |
| 210 printed circuit board |
| 212 electronic components |
| 214 electrical connections |
| 220 support fixture |
| 230 positioning table |

-continued

| Reference Numerals in Drawings |
| --- |
| 240 rotating X-ray detector |
| 250 fluorescent screen |
| 252 first mirror |
| 254 second mirror |
| 256 turntable |
| 258 camera |
| 260 feedback system |
| 262 input connection |
| 263 sensor |
| 264 output connection |
| 265 position encoder |
| 270 computer |
| 276 input line |
| 278 output line |
| 280 rotating source spot |
| 281 deflection coils |
| 282 X-rays |
| 283 region of circuit board |
| 284 X-rays |
| 285 rotating electron beam |
| 286 light |
| 287 target anode |
| 290 granite support table |
| 292 load/unload port |
| 294 operator station |
| 300 two component assembly |
| 310 first material |
| 320 second material |
| 330 incident X-rays |
| 350 X-ray image |
| 360 foreground image region |
| 370 background image regions |
| 410 (BG,ΔG) calibration points |
| 420 linear fit to $t_1$ calibration data |
| 430 linear fit to $t_2$ calibration data |
| 440 linear fit to $t_3$ calibration data |
| 450 unknown thickness line |
| 510 hyperbolic calibration curve |
| 512 calibration data points |
| 520 hyperbolic calibration curve |
| 514 calibration data points |
| 530 hyperbolic data curve |

DETAILED DESCRIPTION OF THE PREFERRED EMBODIMENTS

RELATIONSHIP BETWEEN SOLDER THICKNESS AND X-RAY IMAGE GRAY LEVEL

While the following description is presented in terms of a two component assembly comprising a layer of solder and a layer of copper, it is to be understood that the present invention also applies to any two component assembly. It is to be further understood that the present invention applies equally to a three component assembly where one of the three components is unchanging (e.g., the G10 substrate of a printed circuit assembly). Since the effect of the unchanging third component is simply to alter the source intensity spectrum, it is not explicitly treated in the following description. Furthermore, the two components need not be in distinct layers but may be intermixed. One skilled in the art will recognize that the terms "gray level" and "intensity", as used throughout, are closely related and are often interchangeable. In general, "gray level" refers to an X-ray detector measured X-ray intensity which is converted to an arbitrary scale of gray levels. Thus, a specific gray level is functionally related to a corresponding X-ray intensity. Similarly, one skilled in the art will recognize that the terms "attenuation" and "absorption" with reference to X-rays, are closely related and are often used interchangeably in the literature. Generally, "attenuation" usually includes both "absorption" and "scattering" of X-rays, and is the parameter of interest herein, without regard to whether it is caused by absorption or scattering. However, since the terms are frequently interchanged in the art, "absorption" may sometimes also be used to include both "absorption" and "scattering" of X-rays. If a distinction is significant, one skilled in the art will generally be able to determine the correct intention by reference to the context in which the terms are used.

In an X-ray image of solder material, typically a combination of lead and tin, there is a relationship between the intensities comprising the X-ray image and the thicknesses of the solder material forming the X-ray image. FIG. 1A illustrates an example of this general relationship. In this example, it is seen that the image intensity increases from values corresponding to lighter shades of gray (white) to values corresponding to darker shades of gray (black) as the thickness of the solder material increases. That is, the image of a thin section of solder will have a gray level that is less than the gray level of the image of a thicker section of solder. The image of the thin section will appear to be a lighter shade of gray than the image of the thicker section. (This convention is typically used in electronic image representation of X-ray images, however, the opposite convention may also be used, i.e., where the image of a thin section of solder has a gray level that is greater than the gray level of the image of a thicker section of solder. The latter convention has traditionally been followed in film radiography where the X-ray images are recorded on X-ray film. The present invention may be implemented using either convention.) Additionally, in the following description, the gray scale ranges from zero to a maximum value where the lower values correspond to the lighter shades of gray (white) and the values near the maximum value correspond to darker shades of gray (black). It is to be understood that other conventions for representing the gray scale may also be used. For example, lower values may be selected to correspond to the darker shades of gray (black) and the values near the maximum value may be selected to correspond to lighter shades of gray (white).

SOLDER THICKNESS DETERMINATION USING CALIBRATION STEP WEDGE

Figure 1B:
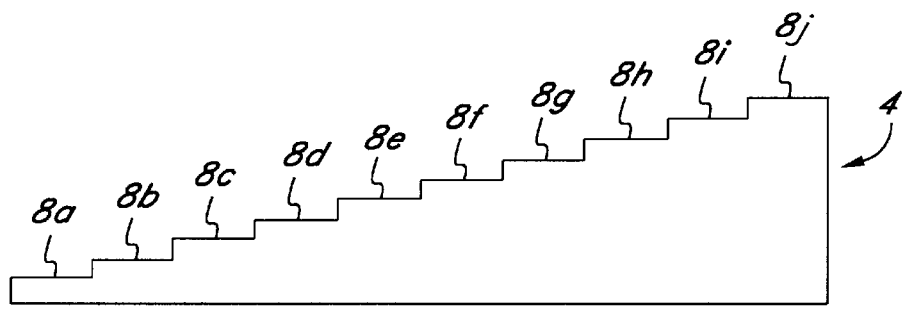
FIG. 1B shows a calibration step wedge of solder material used for calibrating the gray scale image intensity versus thickness relationship for X-ray images of the solder material.
Figure 1C:
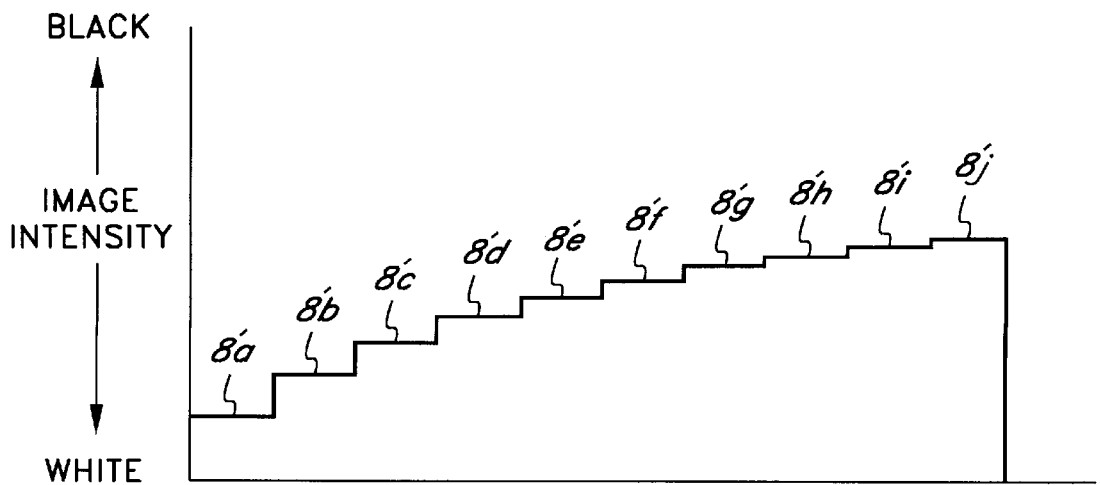
FIG. 1C is a graphical representation of the gray scale image intensity versus thickness relationship for the solder material calibration step wedge shown in FIG. 1B.

The relationship between solder thickness and image gray level may be calibrated using a calibration step wedge comprising multiple steps of differing thickness. An example of such a step wedge 400 is shown in FIG. 1B. Step wedge 400 is constructed of solder material and comprises ten steps 8 having thicknesses ranging from 0.001 inch to 0.010 inch in increments of 0.001 inch. It is possible to construct the step wedge 4 with other dimensions (e.g., in 2 mil increments from 2 mils to 20 mils, etc.), depending upon the thicknesses of the solder joints and the type of circuit board that is to be inspected. An X-ray image of the step wedge 4 exhibits an image intensity 8' versus solder thickness relationship as shown in FIG. 1C. Since the thicknesses of the steps 8 are known, the corresponding intensities 8' may be compared to intensities of other X-ray images of solder material where the thicknesses are not known to determine the unknown thicknesses. Alternative methods of calibrating the solder thickness of a step wedge to correspond to various image intensities may yield more accurate results than this technique.

In the case of circuit board assemblies, the solder is attached to a circuit board. Thus, gray scales displayed in the X-ray images include contributions from the solder as well as the material comprising the circuit board. Typically the circuit board substrate is a plastic or resin type material and may further include ground planes and circuit traces made of a conducting material, e.g., copper. In these cases, determination of the solder thickness is complicated by the presence of the circuit board and associated materials which contribute to a background in the X-ray images. Background shading correction techniques for removing the contribution due to a background are described below.

An alternative calibration standard for solder thickness calibration measurements comprises multiple isolated dots or circular regions of solder of differing known thicknesses attached to an epoxy/plastic substrate typical of a circuit board, e.g., a G-10 material. Typically, the gray level of the portion of the X-ray image of the calibration standard corresponding to the central region of each dot/circular region of solder is selected as being representative of the gray level of the entire dot/circular region to eliminate possible errors due to edge effects, etc.

X-RAY IMAGE FORMATION

Figure 2:
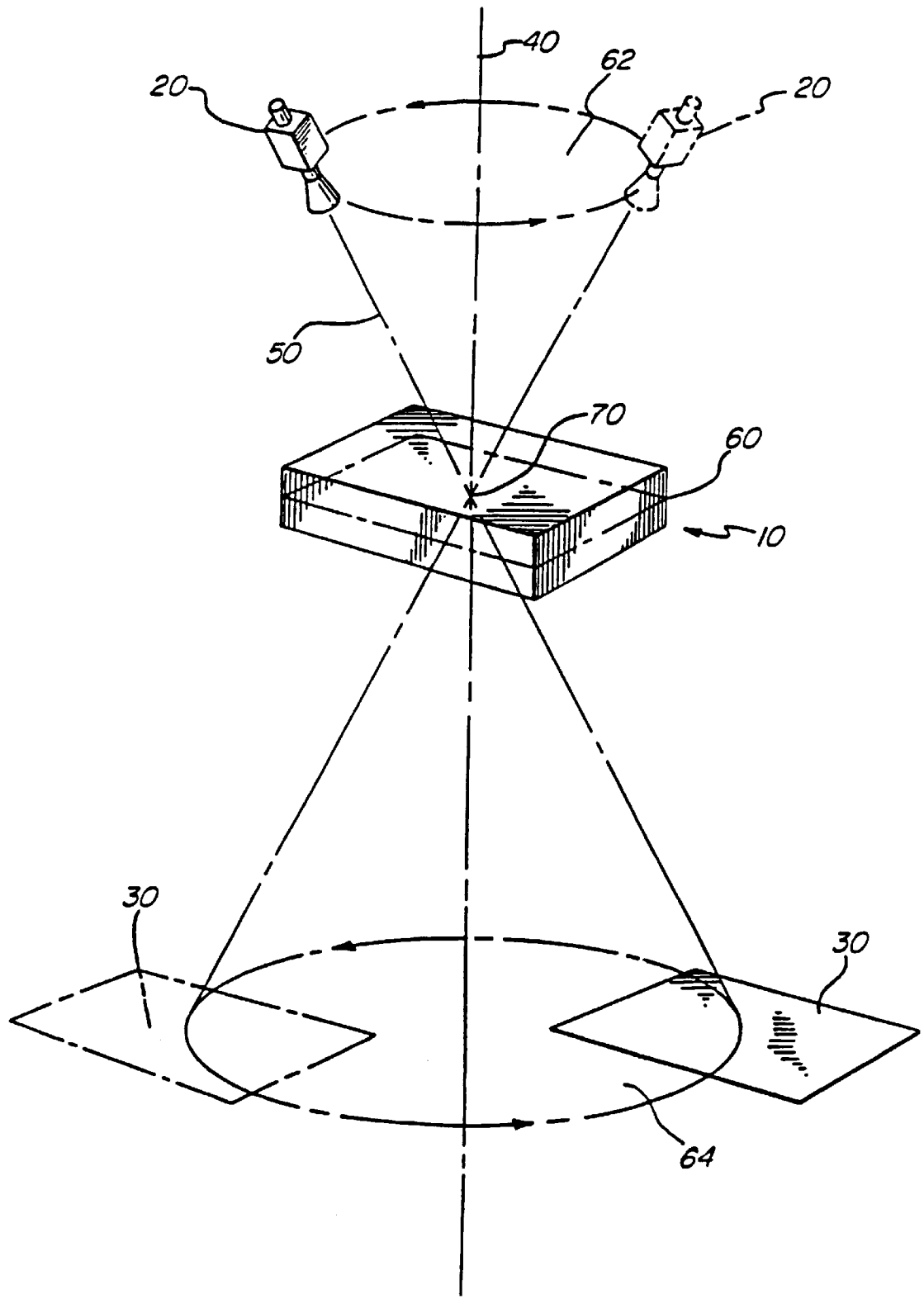
FIG. 2 is a schematic representation of a laminography system illustrating the principles of the technique.

FIG. 2 shows a schematic representation of a typical laminographic geometry which may be used with the present invention. An object 10 under examination, for example, a circuit board, is held in a stationary position with respect to a source of X-rays 20 and an X-ray detector 30. Synchronous rotation of the X-ray source 20 and detector 30 about a common axis 40 causes an X-ray image of the plane 60 within the object 10 to be formed on the detector 30. The image plane 60 is substantially parallel to the planes 62 and 64 defined by the rotation of the source 20 and detector 30, respectively. The image plane 60 is located at the intersection 70 of a central ray 50 from the X-ray source 20 and the common axis of rotation 40. This point of intersection 70 acts as a fulcrum for the central ray 50, thus causing an in-focus cross-sectional X-ray image of the object 10 at the plane 60 to be formed on detector 30 as the source and detector synchronously rotate about the intersection point 70. Structure within the object 10 which lies outside of plane 60 forms a blurred X-ray image on detector 30.

In the laminographic geometry shown in FIG. 2, the axis of rotation of the radiation source 20 and the axis of rotation of the detector 30 are coaxial. However, it is not necessary that these axes of rotation of the radiation source 20 and the detector 30 be coaxial. The conditions of laminography are satisfied and a cross-sectional image of the layer 60 will be produced as long as the planes of rotation 62 and 64 are mutually parallel, and the axes of rotation of the source and the detector are mutually parallel and fixed in relationship to each other. Coaxial alignment reduces the number of constraints upon the mechanical alignment of the apparatus. It is to be understood that the present invention is not limited to any specific laminographic configuration. One skilled in the art will recognize that there are numerous alternative configurations for generating laminographic images which may also be used. Furthermore, the present invention is not limited to cross-sectional images of a two component assembly, but may be practiced with any type of X-ray image of the assembly, including but not limited to laminographic images, CT images, shadow graph images, etc.

FIGS. 3A–3E show laminographs produced by the above described laminographic technique. The object 10 shown in FIG. 3A has test patterns in the shape of an arrow 81, a circle 82 and cross 83 embedded within the object 10 in three different planes 60a, 60b and 60c, respectively.

Figure 3A:
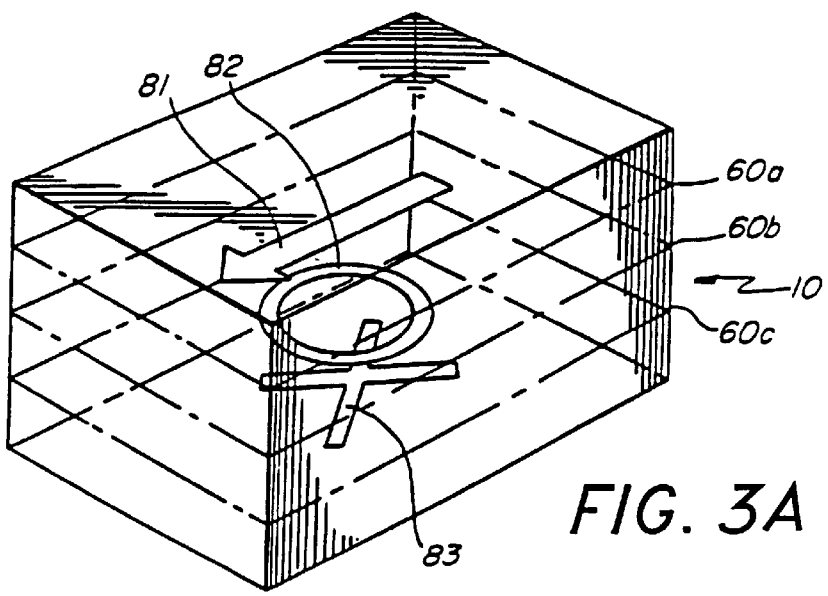
FIG. 3A shows an object having an arrow, a circle and a cross embedded in the object at three different planar locations.
Figure 3B:
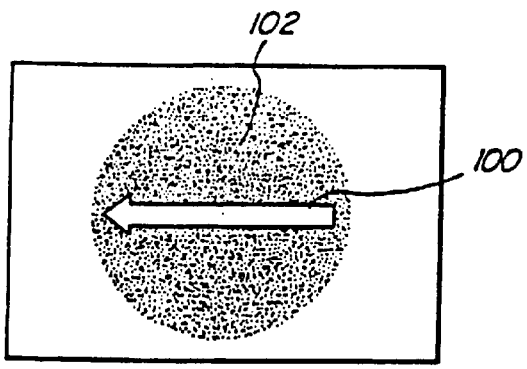
FIG. 3B shows a laminograph of the object in FIG. 3A focused on the plane containing the arrow.

FIG. 3B shows a typical laminograph of object 10 formed on detector 30 when the point of intersection 70 lies in plane 60a of FIG. 3A. The image 100 of arrow 81 is in sharp focus, while the images of other features within the object 10, such as the circle 82 and cross 83 form a blurred region 102 which does not greatly obscure the arrow image 100.

Figure 3D:
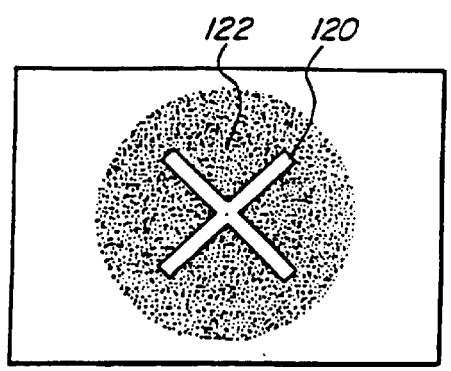
FIG. 3D shows a laminograph of the object in FIG. 3A focused on the plane containing the cross.
Figure 3C:
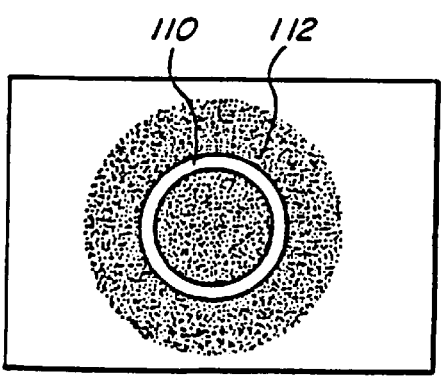
FIG. 3C shows a laminograph of the object in FIG. 3A focused on the plane containing the circle.

Similarly, when the point of intersection 70 lies in plane 60b, the image 110 of the circle 82 is in sharp focus as seen in FIG. 3C. The arrow 81 and cross 83 form a blurred region 112.

FIG. 3D shows a sharp image 120 formed of the cross 83 when the point of intersection 70 lies in plane 60c. The arrow 81 and circle 82 form blurred region 122.

Figure 3E:
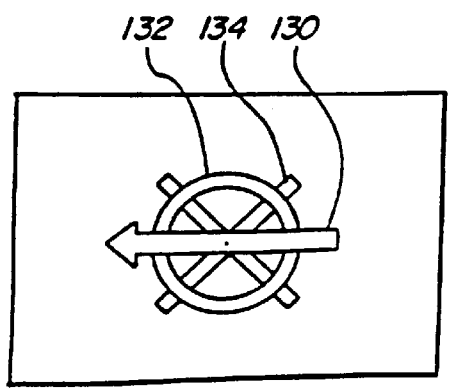
FIG. 3E shows a conventional, two-dimensional X-ray projection image of the object in FIG. 3A.

For comparison, FIG. 3E shows an X-ray shadow image of object 10 formed by conventional projection radiography techniques. This technique produces sharp images 130, 132 and 134 of the arrow 81, circle 82 and cross 83, respectively, which overlap one another. FIG. 3E vividly illustrates how multiple characteristics contained within the object 10 may create multiple overshadowing features in the X-ray image which obscure individual features of the image.

FIG. 4A illustrates a schematic diagram of a typical laminographic apparatus usable with the present invention. In this configuration, an object under inspection is a printed circuit board 210 having multiple electronic components 212 mounted on the board 210 and electrically interconnected via electrical connections 214 (See FIG. 4B). Typically, the electrical connections 214 are formed of solder. However, various other techniques for making the electrical connections 214 are well known in the art and even though the invention will be described in terms of solder joints, it will be understood that other types of electrical connections 214 including, but not limited to, conductive epoxy, mechanical, tungsten and eutectic bonds may be inspected utilizing the invention. FIG. 4B, which is a top view enlargement of a region 283 of the circuit board 210, more clearly shows the components 212 and solder joints 214.

The laminographic apparatus acquires cross-sectional images of the solder joints 214 using the previously described laminographic method or other methods capable of producing equivalent cross-sectional images. The cross-sectional images of the solder joints 214 are automatically evaluated to determine their quality and physical characteristics, including, e.g., solder thickness. Based on the evaluation, a report of the solder joint quality and physical characteristics is presented to the user.

The laminographic apparatus, as shown in FIG. 4A, comprises an X-ray tube 200 which is positioned adjacent printed circuit board 210. The circuit board 210 is supported by a fixture 220. The fixture 220 is attached to a positioning table 230 which is capable of moving the fixture 220 and board 210 along three mutually perpendicular axes, X, Y and Z. A rotating X-ray detector 240 comprising a fluorescent screen 250, a first mirror 252, a second mirror 254 and a turntable 256 is positioned adjacent the circuit board 210 on the side opposite the X-ray tube 200. A camera 258 is positioned opposite mirror 252 for viewing images reflected into the mirrors 252, 254 from fluorescent screen 250. A feedback system 260 has an input connection 262 from a sensor 263 which detects the angular position of the turntable 256 and an output connection 264 to X and Y deflection coils 281 on X-ray tube 200. A position encoder 265 is attached to turntable 256. The position sensor 263 is mounted adjacent encoder 265 in a fixed position relative to the axis of rotation 40. The camera 258 is connected to a computer 270 via an input line 276. The computer 270 includes the capability to perform high speed image analysis. An output line 278 from the computer 270 connects the computer to positioning table 230.

Figure 4C:
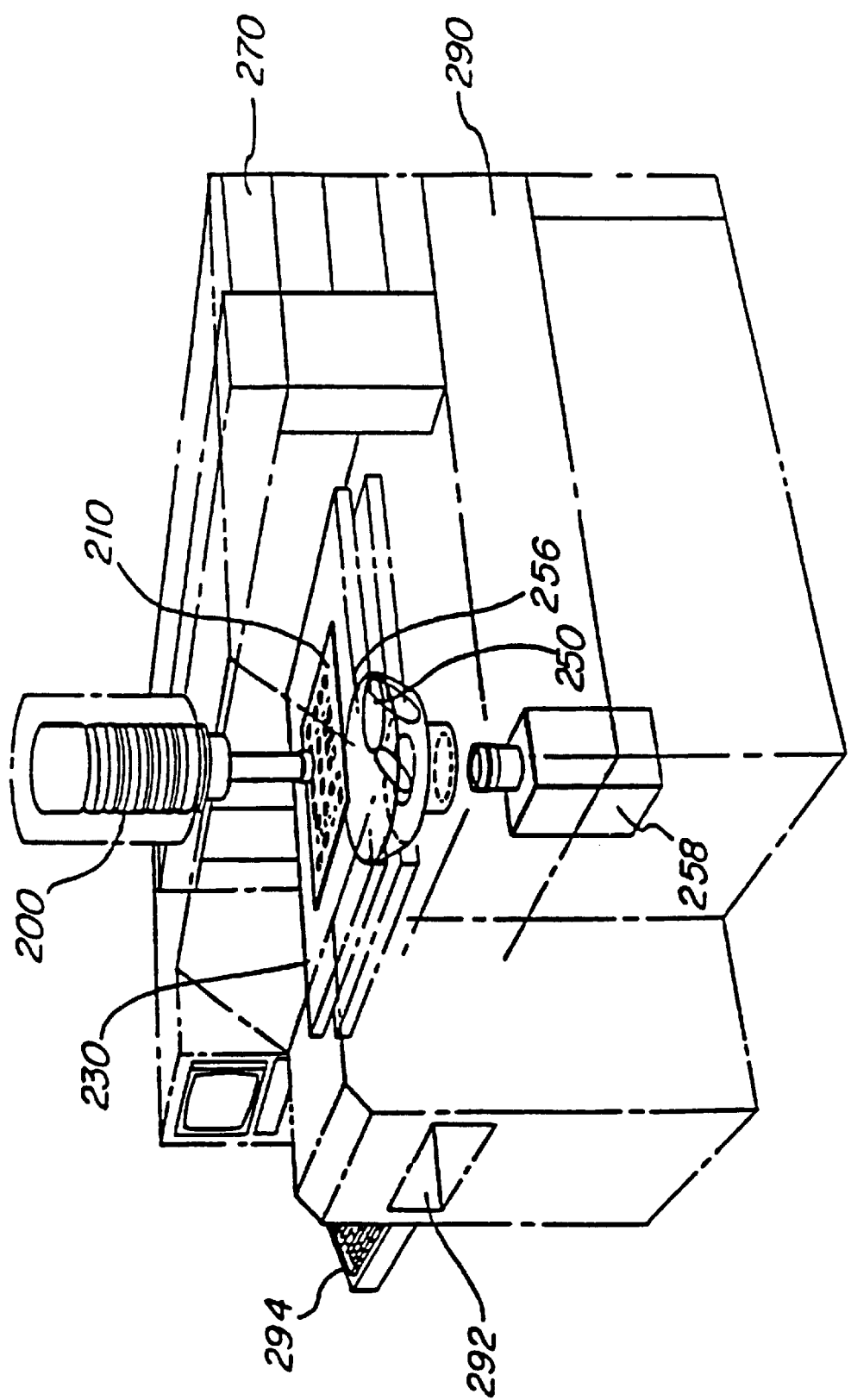
FIG. 4C is a perspective view of the circuit board inspection laminography system shown in FIG. 4A.

A perspective view of the laminographic apparatus is shown in FIG. 4C. In addition to the X-ray tube 200, circuit board 210, fluorescent screen 250, turntable 256, camera 258, positioning table 230 and computer 270 shown in FIG. 4A, a granite support table 290, a load/unload port 292 and an operator station 294 are shown. The granite table 290 provides a rigid, vibration free platform for structurally integrating the major functional elements of the laminographic apparatus, including but not limited to the X-ray tube 200, positioning table 230 and turntable 256. The load/unload port 292 provides a means for inserting and removing circuit boards 210 from the machine. The operator station 294 provides an input/output capability for controlling the functions of the laminographic apparatus as well as for communication of inspection data to an operator.

In operation of the laminographic apparatus as shown in FIGS. 4A and 4C, high resolution, cross-sectional X-ray images of the solder joints 214 connecting components 212 on circuit board 210 are acquired using the X-ray laminographic method previously described in reference to FIGS. 2 and 3. Specifically, X-ray tube 200, as shown in FIG. 4A, comprises a rotating electron beam spot 285 which produces a rotating source 280 of X-rays 282. The X-ray beam 282 illuminates a region 283 of circuit board 210 including the solder joints 214 located within region 283. X-rays 284 which penetrate the solder joints 214, components 212 and board 210 are intercepted by the rotating fluorescent screen 250.

Dynamic alignment of the position of the X-ray source 280 with the position of rotating X-ray detector 240 is precisely controlled by feedback system 260. The feedback system correlates the position of the rotating turntable 256 with calibrated X and Y deflection values stored in a look-up table (LUT). Drive signals proportional to the calibrated X and Y deflection values are transmitted to the steering coils 281 on the X-ray tube 200. In response to these drive signals, steering coils 281 deflect electron beam 285 to locations on a target anode 287 such that the position of the X-ray source spot 280 rotates in synchronization with the rotation of detector 240 in the manner previously discussed in connection with FIG. 2.

X-rays 284 which penetrate the board 210 and strike fluorescent screen 250 are converted to visible light 286, thus creating a visible image of a single plane within the region 283 of the circuit board 210. The visible light 286 is reflected by mirrors 252 and 254 into camera 258. Camera 258 typically comprises a low light level closed circuit TV (CCTV) camera which transmits electronic video signals corresponding to the X-ray and visible images to the computer 270 via line 276. The image analysis feature of computer 270 analyzes and interprets the image to determine the quality of the solder joints 214.

Computer 270 includes one or more processors, one or more memories and various input and output devices including but not limited to monitors, disk drives, printers and keyboards. It is to be understood that the image analysis methods of the present invention may be implemented in a variety of ways by one skilled the art, however, implementation with the computer or specially dedicated image processor is preferred. Additionally, it is to be understood that the term "image" is not limited to formats which may be viewed visually, but may also include digital or analog representations which may be acquired, stored and analyzed by the computer.

Computer 270 also controls the movement of positioning table 230 and thus circuit board 210 so that different regions of circuit board 210 may be automatically positioned within inspection region 283.

The laminographic geometry and apparatus shown and described with reference to FIGS. 2–4 are typical of that which may be used in conjunction with the present invention. However, specific details of these systems are not critical to the practice of the present invention, which addresses the accurate measurement of the thickness of a solder joint positioned on a circuit board 210. For example, the number of computers and delegation of tasks to specific computers may vary considerably from system to system as may the specific details of the X-ray source, detector, circuit board positioning mechanism, etc. More detailed descriptions of laminography systems may be found in the following U.S. Pat. Nos.: 4,926,452; 5,097,492; 5,081,656; 5,291,535; 5,621,811; 5,561,696; 5,199,054; 5,259,012; 5,583,904; and 5,687,209, previously incorporated herein by reference.

One skilled in the art will also recognize that other techniques, for example computed tomography, may be used to produce cross sectional images of specific planes within a solder joint. It is also to be understood that the present invention may be practiced using conventional X-ray shadowgraph images (See FIG. 3E) of solder joints on circuit boards or other multiple component assemblies. Furthermore, specific details of various techniques and equipment for creating the cross-sectional or shadowgraph X-ray images of the multiple component assemblies being inspected may be utilized. The present invention is applicable to any type of system which derives the thickness or relative quantity of a first material in the presence of a second material from an analysis of the gray levels comprising an X-ray image of the assembly.

PHYSICS OF X-RAY ATTENUATION

Figure 5:
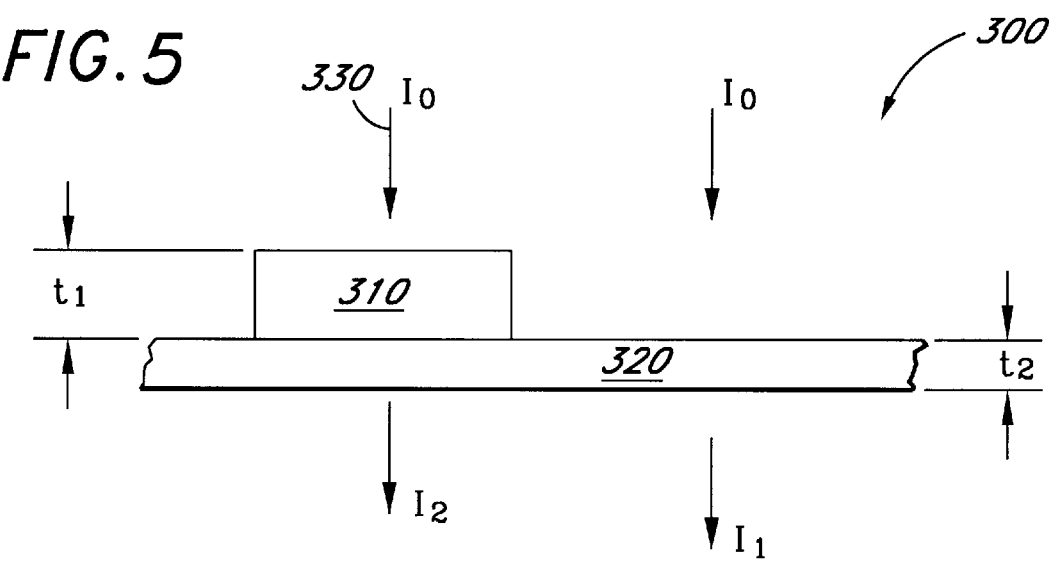
FIG. 5 shows a schematic cross sectional representation of a portion of a two component assembly 300 comprising a first material 310 (e.g., solder) in combination with a second material 320 (e.g., copper, plastic, etc).

FIG. 5 shows a schematic cross sectional representation of a portion of a two component assembly 300 comprising a first material 310 (e.g., solder) in combination with a second material 320 (e.g., copper, plastic, etc). U.S. Pat. No. 5,291,535 discusses various techniques for calibrating such configurations including 1) a background subtraction (additive component); and 2) a combination background subtraction followed by a multiplicative component. While these approaches may be adequate for certain applications, other applications require more accurate techniques for deriving a solder thickness measurement from an X-ray image in the presence of a background material. The linear shading correction method described below has been found to provide significant improvement over the additive and additive/multiplicative corrections described in U.S. Pat. No. 5,291,535.

As shown in FIG. 5, X-rays 330 having a incident intensity $I_0$, are directed upon the assembly 300 from a first side and encounter regions of the assembly 300 which include the first material 310 having a thickness $t_1$ in combination with the second material 320 having a thickness $t_2$, and other regions of the assembly 300 which include only the second material 320. In regions where the X-rays have passed through only the second material 320, the incident intensity $I_0$ is attenuated to an intensity $I_1$. Similarly, in regions where the X-rays have passed through both the first material 310 and the second material 320, the incident intensity $I_0$ is attenuated to an intensity $I_2$. The absorption of monochromatic X-rays in the region including only the second material 320 is governed by the following relation:

$$I_1 = I_0 e^{-\alpha_2 t_2} \quad (1)$$

where $\alpha_2$ is is the X-ray attenuation coefficient for the second material 320. The absorption of monochromatic X-rays in the region including both the first material 310 and the second material 320 is governed by the following relation:

$$I_2 = I_0 e^{-\alpha_1 t_1} e^{-\alpha_2 t_2} \quad (2)$$

where $\alpha_1$ is the X-ray attenuation coefficient for the first material 310.

FIG. 5 illustrate s the X-rays 330 passing through the assembly 300 in a direction which is perpendicular to the first and second layers 310 and 320, thus, $t_1$ and $t_2$ represent the thicknesses of the first and second layers 310 and 320, respectively. In the event the X-rays pass through the assembly at some other angle, $t_1$ and $t_2$ represent the distances the X-rays have travelled through the first and second layers 310 and 320, respectively.

SOLDER THICKNESS DETERMINATION USING LINEAR SHADING CORRECTIONS

As previously discussed, X-ray inspection of printed circuit assemblies typically produces gray-scale images of interconnects or slices thereof which are analyzed and examined to detect and classify improper joints and/or to provide statistical process control data relating to the manufacturing process. It is desirable that measurements taken relate directly to physical characteristics of the joint under inspection. For example, in characterizing solder joints, it is preferable to deal with measured joint thickness, i.e., solder thickness, rather than gray scale pixel values. The following described linear shading correction technique has previously been used for converting the solder image gray scale pixel values to solder thicknesses. Since the present invention is an enhancement and extension of this linear shading correction method, a summary description is presented to facilitate the understanding of the present invention.

Figure 6:
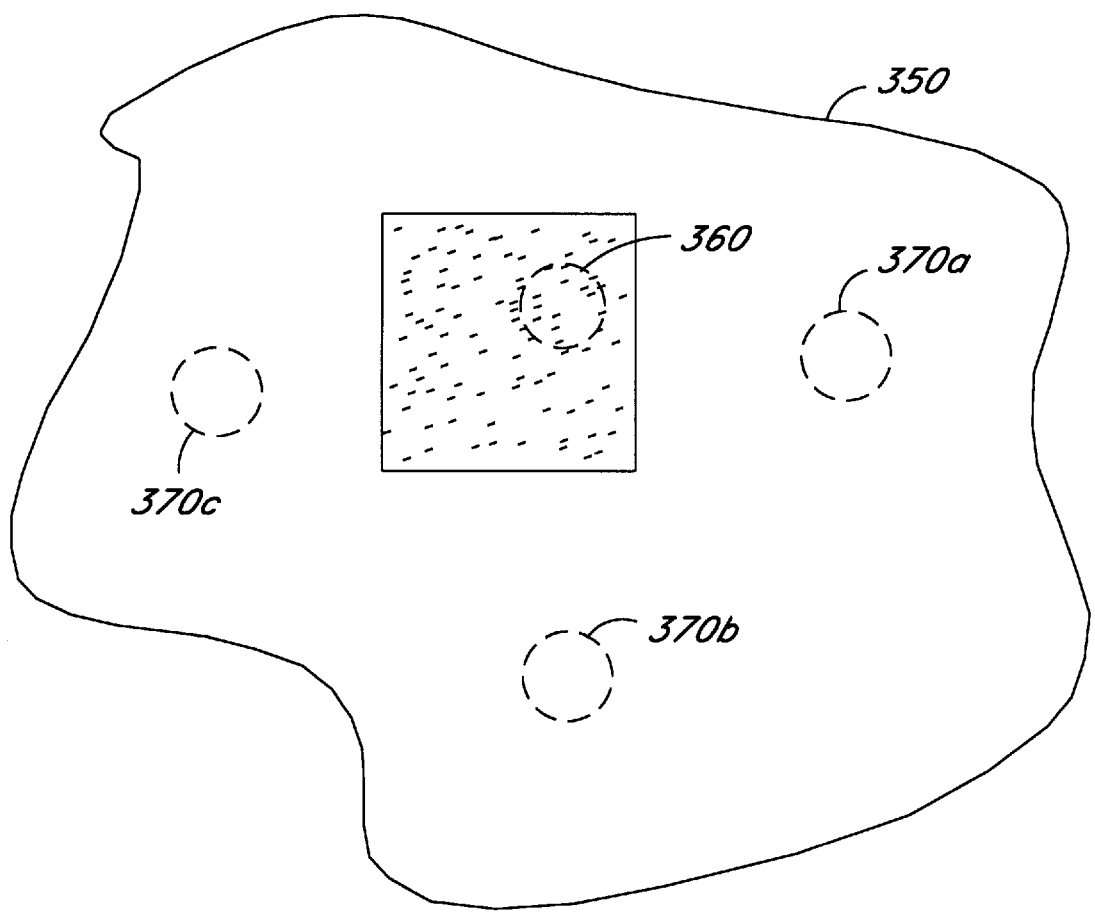
FIG. 6 shows a plan view representation of an X-ray image of the two component assembly 300 shown in FIG. 5.

Shown in FIG. 6 is a plan view representation of an X-ray image 350 of the two component assembly 300 shown in FIG. 5 where the first material 310 is solder and the second material 320 is copper or a combination of copper and circuit board materials. A foreground image region 360 is representative of a portion of a typical X-ray image of a solder pad, i.e., the first material 310 (e.g., solder) in combination with the second material 320 (e.g., copper). Similarly, background regions 370 are representative of portions of a typical X-ray image of a circuit board substrate, i.e., the second material 320 (e.g., copper, plastic, etc). A gray scale level which is representative of the gray level due to the solder, $\Delta G_i$, is obtained by subtracting a background (copper) gray level $B_i$, i.e., the gray level of the X-ray image in regions 370, from a foreground (solder+copper) gray level $F_i$, i.e., the gray level of the X-ray image in region 360, as follows:

$$\Delta G_i = F_i - B_i \quad (3)$$

The linear shading correction technique is based on the following two assumptions:
1) Plots of Delta Gray level due to solder at constant solder thickness ($\Delta G$) vs. Background Gray Level (BG) may be approximated by a series of straight lines intersecting the Background axis at a single point; and
2) At a "nominal" or reference background gray level (e.g., zero) the Delta Gray level due to solder ($\Delta G$) vs. Solder Thickness (t), function may be approximated by a fitted curve of known form, e.g., a sum of exponentials. In the following examples, a reference background gray level of zero was selected for convenience. However, it is to understood that other non-zero reference background gray levels may be selected.

Figure 7:
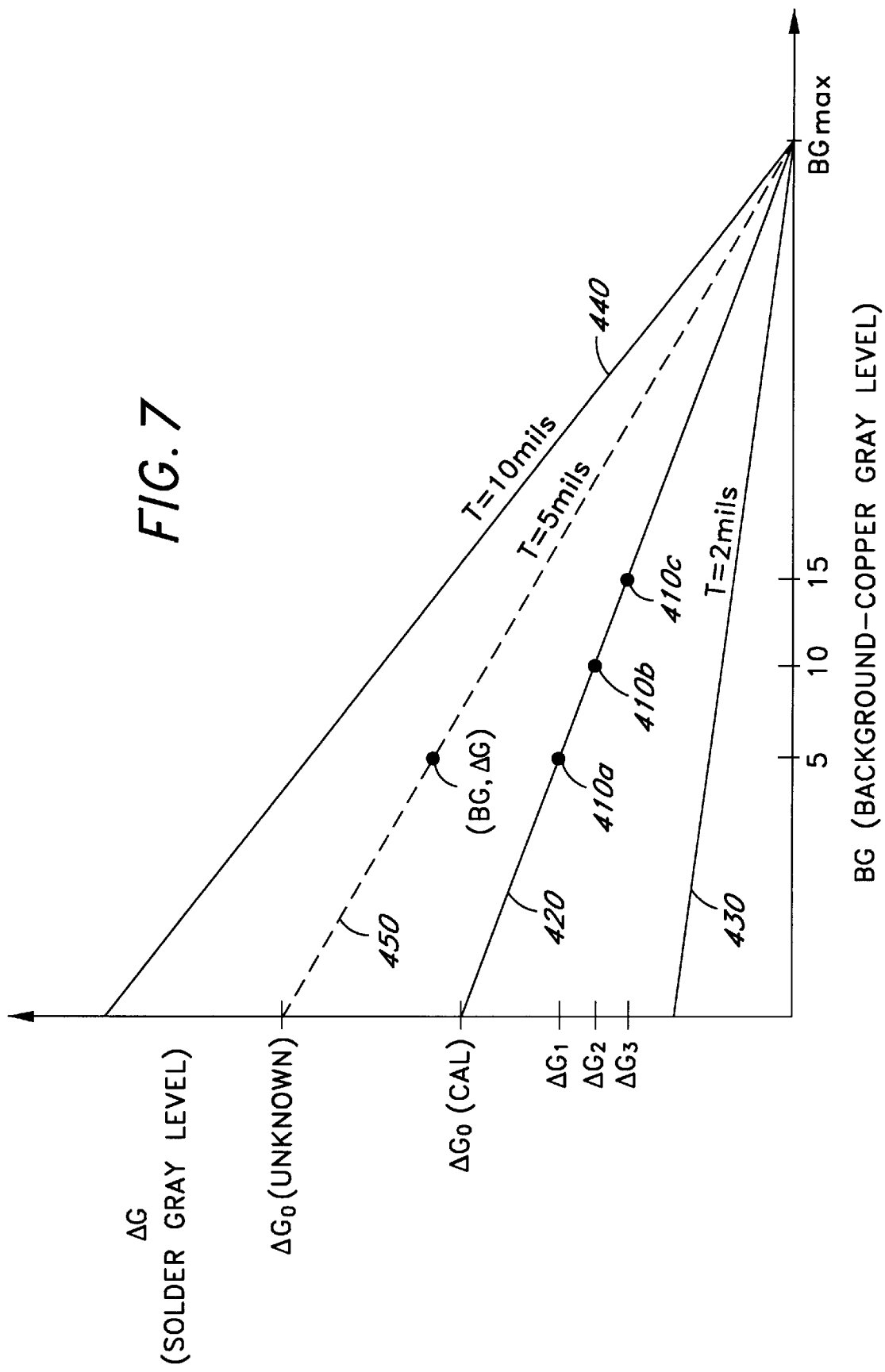
FIG. 7 illustrates linear plots of Delta Gray Level due to solder having a constant solder thickness ($\Delta G$) vs. Background Gray Level (BG).

In accordance with assumption 1) of the linear shading correction technique, three values of $\Delta G_i$ for a constant value of solder thickness in the presence of three different thicknesses of copper are obtained. Shown in FIG. 7 is a plot of an example where a solder thickness of 4 mils is shielded by copper having thicknesses of 5, 10 and 15 mils. Calibration data points 410a, 410b and 410c correspond to (BG,$\Delta$G) coordinates (5,$\Delta G_1$), (10,$\Delta G_2$) and (15,$\Delta G_3$), respectively. These values of solder and copper thicknesses are selected for purposes of illustration only. Different thickness values and materials may be used for particular applications. Fitting a straight line 420 to the points 410a, 410b and 410c determines a BG-axis intercept of $BG_{MAX}$ and a $\Delta G$-axis intercept of $\Delta G_0$(Cal). The linear function describing straight line 420 is:

$$\Delta G = -\frac{\Delta G_0(CAL)}{BG_{MAX}} BG + \Delta G_0(CAL) \quad (4)$$

where the constants $BG_{MAX}$ and $\Delta G_0$(CAL) are determined from the linear fit to calibration points 410a, 410b and 410c.

As stated previously, the linear shading correction technique assumes that plots of Delta Gray level due to solder at different constant solder thicknesses will form a series of straight lines intersecting the Background-axis at the same point, $BG_{MAX}$. In accordance with this assumption, straight lines 430 and 440 represent plots of $\Delta G$ vs. BG for solder thicknesses of 2 mils and 10 mils, respectively (individual data points not shown for lines 430 and 440).

Thus, for any set of measured coordinates, (BG,$\Delta$G), corresponding to an unknown solder thickness, $t_U$, the solder delta gray level at a "nominal" or reference background gray level (e.g., zero) $\Delta G_0$(UNKNOWN), is the $\Delta G$-axis intercept of a straight line 450 determined by the measured coordinates (BG,$\Delta$G) and the BG-axis intercept, ($BG_{MAX}$,0). The linear function describing straight line 450 is:

$$\Delta G = -\frac{\Delta G_0(UNKNOWN)}{BG_{MAX}} BG + \Delta G_0(UNKNOWN) \quad (5)$$

Using the measured data (BG,$\Delta$G), corresponding to the unknown solder thickness $t_U$, the unknown $\Delta G$-axis intercept, $\Delta G_0$(UNKNOWN), may be determined by rearrangement of equation (5) as follows:

$$\Delta G_0(UNKNOWN) = \frac{\Delta G}{1 - \frac{BG}{BG_{MAX}}} \quad (6)$$

Applying assumption 2) of the linear shading correction technique, the unknown solder thickness $t_U$ may then be determined by using the solder delta gray level at a "nominal" or reference background gray level (e.g., zero) for the unknown solder thickness, $\Delta G_0$(UNKNOWN), in the following functional relationship:

$$\Delta G_0(UNKNOWN) = A(1 - e^{-k_1 t_U}) + B(1 - e^{-k_2 t_U}) \quad (7)$$

where fitting constants A, B, $k_1$ and $k_2$ have been previously determined using calibration data.

In summary, the measured data point (BG,$\Delta$G) corresponding to the unknown solder thickness $t_U$, is used in equation (6) to calculate the unknown ΔG-axis intercept, $\Delta G_0$(UNKNOWN), for the unknown thickness $t_U$. Equation (7) is then used to calculate the value of the unknown thickness $t_U$. Alternatively, equation (7) may be used to generate a look up table (LUT) of solder delta gray levels (at a "nominal" or reference background gray level of zero) vs. thickness, to speed up the computation. Since the LUT created from equation (7) comprises multiple pairings of gray levels for solder of various thicknesses corrected to zero background, $\Delta G_0$ and corresponding thicknesses, t, it is a simple matter to find the thickness corresponding to the $\Delta G_0$(UNKNOWN) for any measured data point. That is, once the solder delta gray level at the "nominal" or reference background gray level (zero in this example) $\Delta G_0$ (UNKNOWN) for a measured unknown point (BG,ΔG) is determined using equation (6), the thickness of solder represented by the value of $\Delta G_0$(UNKNOWN) is found in the LUT, where it is paired with the corresponding solder thickness, t. Interpolation between values in the LUT may be used if the value of $\Delta G_0$(UNKNOWN) does not exactly match an entry in the LUT.

It has been found that the linear shading correction method described above may only be accurate over a limited range of thicknesses. The limited accuracy is due to the fact that the actual plots of Delta Gray level due to solder at constant solder thickness (ΔG) vs. Background Gray Level (BG) curves are only approximately linear. Additionally, the BG-axis intercept, $BG_{MAX}$, may change when the X-ray camera settings are changed, (e.g., camera gain, field of view, etc.) thereby requiring a new calibration.

SOLDER THICKNESS DETERMINATION USING A NON-LINEAR SHADING CORRECTION

The present invention uses a non-linear shading correction procedure to improve the accuracy and repeatability of the linear shading correction method described previously. In order to simplify the following discussion of the non-linear shading correction procedure, the special case of solder shaded by copper will be considered. However, it is to be understood that the invention is not limited to this combination of materials and also applies to assemblies having more than two components.

In the present invention, the gray levels of X-ray images of a number of test coupons which contain known thicknesses of solder shaded by varying amounts of copper are measured. By a combination of theoretical and empirical arguments, it has been found that the effect of the shading may be described by a particular nonlinear equation with three free parameters. Moreover, two of the three parameters are found to be characteristics of the AXI system and not functions of the amount of copper or solder in the X-ray beam path. One aspect of the system calibration involves estimation and storage of these two parameters. Foreground and background gray level values from an unknown sample are adequate to fix the third parameter, completely characterizing the shading effect for that sample. As a result, it is possible to use the two stored system parameters and the known functional form of the shading equation to extrapolate to values that would have been measured under "standard" shading conditions. (Typically, "no shading", i.e., zero background, is used as the standard condition). Since any measured sample can be readily converted to standard conditions using this approach, there is no need for a two dimensional thickness calibration. Instead, a simple one dimensional curve suffices, since measurements can always be corrected to zero background.

The non-linear shading correction technique of the present invention is based on the following two assumptions:

1) Plots of Delta Gray Level (y=ΔG=F−B) due to solder at constant solder thickness (y-axis) vs. Background Gray Level (x=B, x-axis) may be approximated by points located on a left branch of a series of hyperbolic curves having two common parameters as follows:
   A) a common x-axis (i.e., BG-axis) value at which each hyperbolic curve assumes its minimum value of y (i.e., ΔG); and
   B) a common x-axis intercept at a maximum background gray level x=$BG_{MAX}$; and
2) At a "nominal" or reference background gray level (e.g., zero), the Delta Gray level due to solder ($y_0$) vs. Solder Thickness (t), function may be approximated by a fitted curve of known form, e.g., a sum of exponentials. In the following examples, a reference background gray level of zero was selected for convenience. However, it is to understood that other non-zero reference background gray levels may be selected.

In accordance with assumption 1) of the non-linear shading correction technique, each of multiple sets of calibration data are jointly fit to hyperbolic functions of the following form:

$$y = \Delta G = \sqrt{(x-a)^2 + b^2} + c \qquad (8)$$

where a is the x-axis coordinate at which y has a minimum value.

Figure 8:
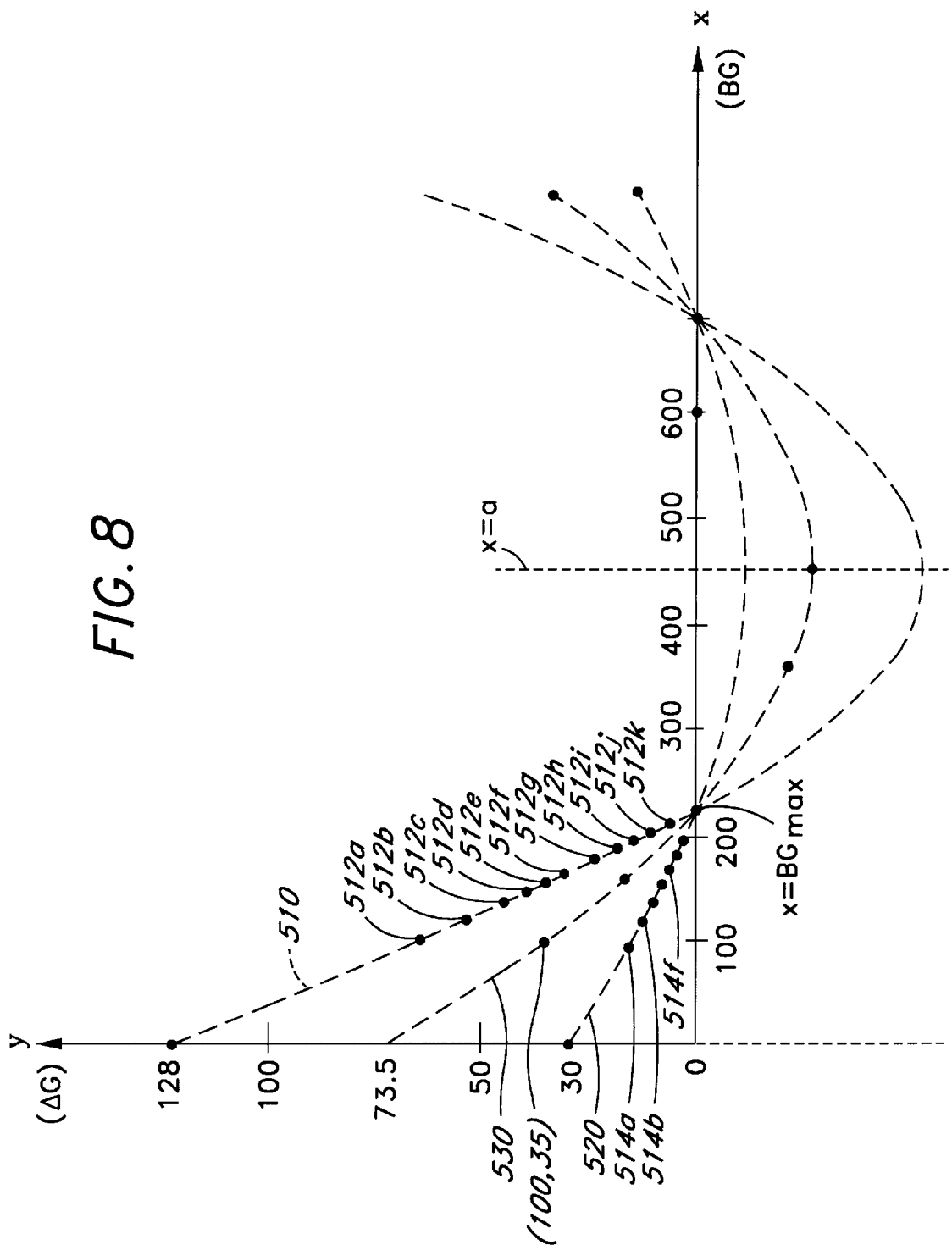
FIG. 8 shows two sets of calibration data and hyperbolic fits to the data illustrating conditions of the non-linear shading correction technique of the present invention.

By way of example, shown in FIG. 8 are a first calibration curve 510 and a second calibration curve 520. The first calibration curve 510 includes multiple calibration data points 512 and the second calibration curve 520 includes multiple calibration data points 514. On the first calibration curve 510, each calibration data point 512 represents a delta gray level for a solder thickness of 7.7 mils in combination with an unknown background material (e.g., unknown thicknesses of circuit board materials including copper) and differing thicknesses of copper background. For example, calibration data point 512a is the delta gray level corresponding to a solder thickness of 7.7 mils of solder in combination with a background copper thickness of 0.0 mils, while calibration data point 512f is the delta gray level corresponding to the 7.7 mils of solder in combination with a copper thickness of 25 mils, etc. Similarly, on the second calibration curve 520, each calibration data point 514 represents a delta gray level for a solder thickness of 1.2 mils in combination with differing background thicknesses of copper. For example, calibration data point 514a is the delta gray level corresponding to a solder thickness of 1.2 mils in combination with a background copper thickness of 0.0 mils, while calibration data point 514f is the delta gray level corresponding to the 1.2 mils of solder in combination with a background copper thickness of 25 mils, etc. Analysis of the first and second calibration curves 510 and 520 by any of a variety of empirical and/or analytical techniques may be used to arrive at a best fit for each hyperbolic calibration curve included in the family of calibration data, with the constraints that each hyperbolic curve has its minimum y-value at the same value of x, i.e., x=a, and each curve has the same x-axis intercept. For the data points shown in FIG. 8, it is seen that curves 510 and 520 which fit the data points 512 and 514, respectively, are obtained by using a value of x=a=455 and an x-axis intercept at x=$BG_{MAX}$=222. As shown in FIG. 8, the first calibration curve 510 is a fit to data points 512 of a hyperbolic function of the form shown in equation (8) where the hyperbolic function represented by calibration curve 510 has a minimum y-value at x=a and intercepts the x-axis at x=$BG_{MAX}$. In accordance with assumption (1), the second calibration curve 520 is a fit to data points 514 of a hyperbolic function of the form shown in equation (8) where the hyperbolic function represented by calibration curve 520 also has a minimum y-value at x=a and also intercepts the x-axis at $x=x_0=BG_{MAX}$. The y-axis intercepts of the fitted calibration curves 510 and 520 are determined by extrapolation of the fitted curves. As shown in this example, the extrapolated y-axis intercept of the first calibration curve 510 is located at approximately $y_0=128$ and the extrapolated y-axis intercept of the second calibration curve 520 is located at approximately $y_0=30$. As previously discussed, the y-axis intercepts of the curves 510 and 520 correspond to "nominal" or reference background gray levels of zero for the respective solder thicknesses represented by the curves 510 and 520. It is noted that the thicknesses of the background copper used to shade the known solder calibration thicknesses need not be known to determine unknown solder thicknesses. However, if it is desired to determine both unknown solder and unknown copper thicknesses, both the solder and copper thicknesses used in the calibration should be known.

After fitting the calibration data 512,514 and obtaining from these fits the values for x=a and $x=x_0=BG_{MAX}$ (a detailed description of two procedures for determining the values for x=a and $x=x_0=BG_{MAX}$ is presented below), which define curves 510 and 520, the value of a delta gray level at a "nominal" background value of zero for an unknown data point (x,y) is obtained as follows. Recall that each calibration curve 510 and 520 is represented by an equation of the form of equation (8) where x=a is the x-axis coordinate at which y (for each calibration curve) has a minimum value. Additionally, all of the calibration curves share a common x-axis intercept at $x=x_0=BG_{MAX}$. Thus, at $x=x_0=BG_{MAX}$, equation (8) becomes $$(BG_{MAX}-a)^2+b^2=c^2 \qquad (9)$$

or $$b^2=c^2-(BG_{MAX}-a)^2=(y-c)^2-(x-a)^2 \qquad (10)$$

Expanding and collecting terms in equation (10) yields the following expression for "c" in terms of "x", "y", "a" and "$BG_{MAX}$":

$$c = \frac{y^2-(x-BG_{MAX})(x+BG_{MAX})+2a(x-BG_{MAX})}{2y} \qquad (11)$$

Thus, for any given unknown data point (x,y), values for "c" and "b" may be calculated from equations (10) and (11). Using the known values of "a", "b" and "c" in equation (8) at x=0 yields the value of $y_0$, i.e., the delta gray level at a "nominal" background value of zero for the unknown data point (x,y). For example, consider an unknown (x,y) data point measurement located at x=BG=100 and y=ΔG=35 for the system having the calibration data 512 and 514 shown in FIG. 8. The delta gray level at a "nominal" background value of zero, $y_0$, for the unknown data point (x,y) is calculated as follows. As previously described in accordance with assumption 1) of the non-linear shading correction technique, a=455 and $BG_{MAX}=222$ for this system. Using these values in equations (11) and (10) yields the values of c=−1,007.3 and b=960,364. Thus, the equation of a hyperbolic curve which includes the measured data point (100,35) on its left branch and has a minimum at x=a=455 and an x-intercept at x=222 is as follows:

$$y=\sqrt{(x-455)^2+960,364}-1,007 \qquad (12)$$

Hyperbolic curve 530 described by equation (12) is shown in FIG. 8. Equation (12) has a y-axis intercept, i.e., delta gray level at a "nominal" background value of zero, of $y_0=73.5$.

As previously stated, analysis of the first and second calibration curves 510 and 520 by any of a variety of empirical and/or analytical techniques may be used to arrive at a best fit for each hyperbolic calibration curve included in the family of calibration data, with the constraints that each hyperbolic curve has its minimum y-value at the same value of x, i.e., x=a, and each calibration curve has the same x-axis intercept, i.e., $x=x_0=BG_{MAX}$. A first procedure utilizes trial and error to combine least squares fits to individual curves, while a second preferred procedure fits all the data simultaneously.

In the trial and error procedure, hyperbolic curves of the form defined by equation (8) are fit to individual sets of calibration data. X-axis intercepts ($x=x_0=BG_{MAX}$) for each of the individual calibration curves are compared and a common value determined by trial and error. Similarly, the x-axis value at which each hyperbolic curve has its minimum y-value, i.e., x=a, may be found by trial and error. Using this value of x=a and a dummy data point at the x-intercept ($x=x_0=BG_{MAX}$), each set of calibration data is re-fit to a calibration curve of the form defined by equation (8). While this procedure may be effective for some applications, it is iterative and somewhat empirical and may not be adequate for production use. Alternatively, a second procedure using non-linear least squares to fit all the data at once may be employed.

In the second procedure, "$x_0$" and "a" are determined by a non-linear least squares fit to the calibration data sets. In this approach, equation (8) is rewritten such that the variables "$b^2$" and "c" are represented in terms of "$x_0$", "a" and "$y_0$", where "$y_0$" is the y-axis intercept of a particular hyperbolic curve. Thus, "$y_0$" varies with each curve in the family while the same values of "$x_0$" and "a" are shared by all of the curves in the family. Thus, at the y-axis intercept $(0,y_0)$ of a particular hyperbola, equations (11), (10) and (8) become:

$$c = \frac{x_0^2+y_0^2-2ax_0}{2y_0} \qquad (13)$$

$$b^2 = c^2-(x_0-a)^2 = \left[\frac{x_0^2+y_0^2-2ax_0}{2y_0}\right]^2-(x_0-a)^2 \qquad (14)$$

$$y = \left[(x-a)^2+\left(\frac{x_0^2+y_0^2-2ax_0}{2y_0}\right)^2-(x_0-a)^2\right]^{1/2} + \frac{x_0^2+y_0^2-2ax_0}{2y_0} \qquad (15)$$

Thus, the derivatives of "y" with respect to "a", "$x_0$" and "$y_0$" are:

$$\frac{dy}{da} = \frac{(x_0-x)y_0-x_0 y}{y_0(y-c)} \qquad (16)$$

$$\frac{dy}{dx_0} = \frac{(x_0-a)(y-y_0)}{y_0(y-c)} \qquad (17)$$

$$\frac{dy}{dy_0} = \frac{y(y_0^2-x_0^2+2ax_0)}{2y_0^2(y-c)} \qquad (18)$$

Note that since "c" is given by a function of "a", "x", and "$y_0$" in equation (13), equations (16), (17) and (18) express the derivatives of "y" as functions of "a", "$x_0$" and "$y_0$".

Thus, equations (8), (16), (17) and (18) express "y" and its derivatives as functions of "a", "$x_0$" and "$y_0$". Using these expressions, fitted values for "a", "$x_0$" and "$y_0$" can be obtained from the calibration data sets using a non-linear least squares fitting technique, for example, the Levenberg-Marquardt technique or other standard non-linear optimization technique. The optimization techniques are used to minimize the sum of square errors (or $X^2$ if variances are known) between the fitted function and the entire set of calibration data points for all of the curves in the family. Examples of optimization techniques may be found in a book entitled "Numerical Recipes for C" authored by Press et al., published by Cambridge University Press in 1992, the entirety of which is hereby incorporated herein by reference.

Applying assumption 2) of the non-linear shading correction technique, the Delta Gray level due to solder ($y_0$) vs. Solder Thickness (t), function may be approximated by a fitted curve of known form, e.g., a sum of exponentials:

$$y_0(t) = p - \Sigma_i q_i e^{-r_i t} \tag{19}$$

where p, $q_i$ and $r_i$ are fitting constants. For example, when the sum of two exponentials is selected, the unknown solder thickness (t) may be determined by using the solder delta gray levels at a "nominal" or reference background gray level of zero ($y_0$) in the following functional form for the sum of two exponentials:

$$y_0(t) = \alpha - \beta e^{-k_1 t} - \gamma e^{-k_2 t} \tag{20}$$

where fitting constants α, β, γ, $k_1$ and $k_2$ are determined by fitting to the calibration data. The 5 fitting parameters can be reduced to three based on the following physical characteristics of the data. At zero solder thickness, the solder delta gray level at a "nominal" background gray level of zero ($y_0$) is zero, i.e., $y_0(0)=0$. The maximum value of the solder delta gray level at a "nominal" background gray level of zero ($y_{0-MAX}$) is $BG_{MAX}$, i.e., $y_{0-MAX}(t \to \infty) = BG_{MAX}$ (based on theoretical and empirical observations). Using this information, the five fitting parameters in equation (20) can be reduced to three since $y_0(0) = \alpha - \beta - \gamma = 0$ and $y_0(t \to \infty) = \alpha = BG_{MAX}$, thus equation (20) becomes $$y_0(t) = BG_{MAX} - \beta e^{-k_1 t} - (BG_{MAX} - \beta) e^{-k_2 t} \tag{21}$$

where fitting constants β, $k_1$ and $k_2$ are determined by fits to the known solder thicknesses and corresponding delta gray levels at a "nominal" background gray level of zero derived from the hyperbolic fits to the calibration data. In applications requiring greater throughput, it may be advantageous to use the above described calibration procedure to generate a look up table (LUT) or surface map of Background (x) vs. Delta Gray (y) vs. Solder Thickness (t).

TYPICAL CALIBRATION DATA AND COMPARISON OF LINEAR VS. NON-LINEAR SHADING CORRECTION TECHNIQUES

The linear and non-linear shading correction techniques described above were applied to multiple solder thickness calibration coupons. The results of these calculations and a comparison of the two techniques is presented below. A solder thickness calibration panel having nine known solder thicknesses was measured with varying thicknesses of copper. The nine solder thicknesses, in mils, were 1.2, 1.6, 3.6, 5.7, 7.7, 9.7, 13.7, 15.6 and 20.0. Delta gray levels as a function of background levels were measured for fifteen different known thicknesses of copper in combination with each of the known solder thicknesses. The fifteen known thicknesses of copper used in these measurements, in mils, were 0, 5, 10, 15, 20, 25, 30, 41, 51, 61, 73, 83, 93, 99 and 110.

Figure 9:
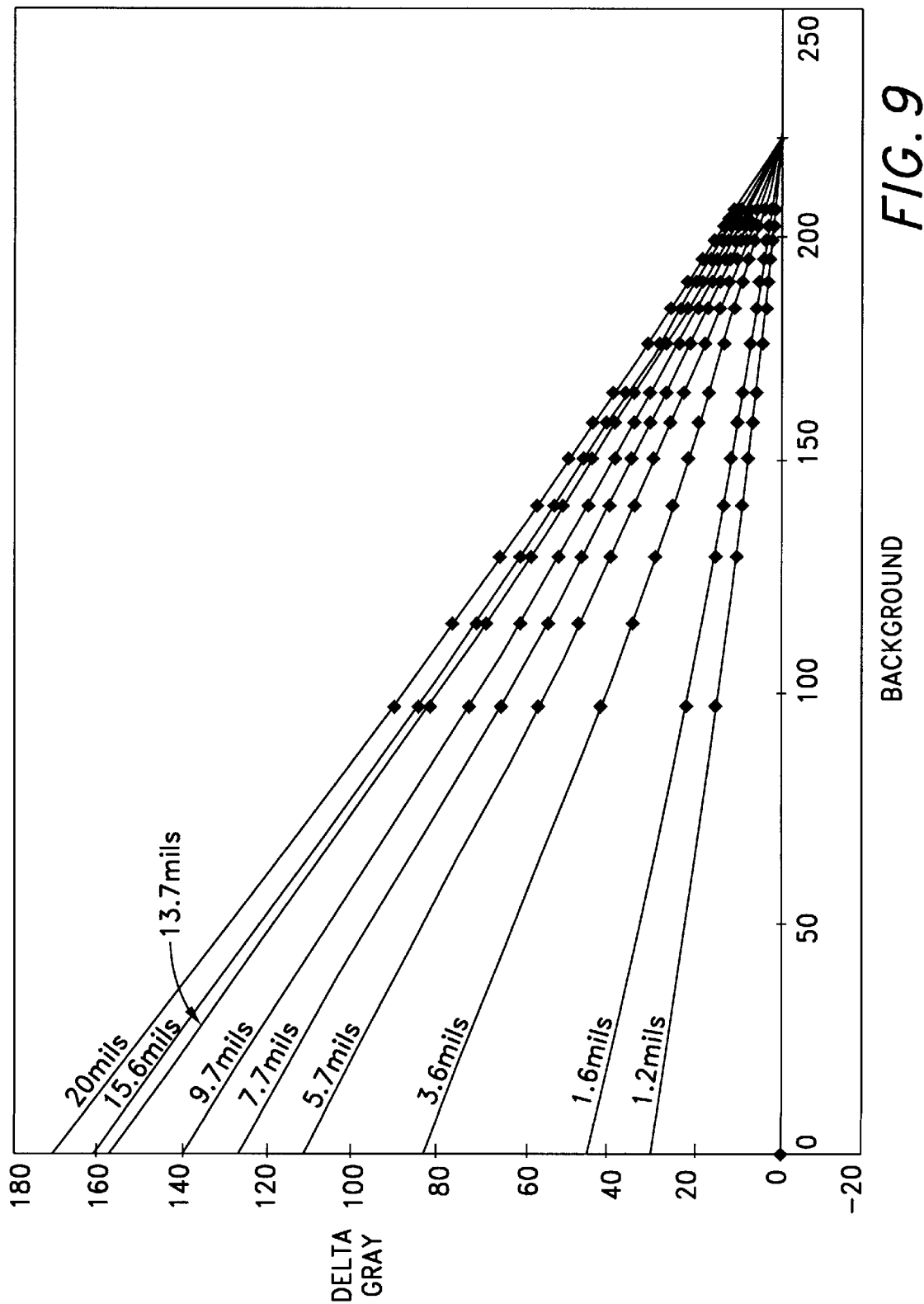
FIG. 9 shows a plot of measured delta gray vs. background levels for 9 sets of calibration data for 9 known solder thicknesses in combination with 15 different known background levels.

FIG. 9 shows a plot of the measured delta gray vs. background levels for these 9 sets of calibration data where the background level was varied by applying the 15 different thicknesses of copper to each solder thickness coupon described above. Also shown in FIG. 9 are nine hyperbolic curves fit to the data points in accordance with assumption 1) of the non-linear shading correction technique.

Figure 10A:
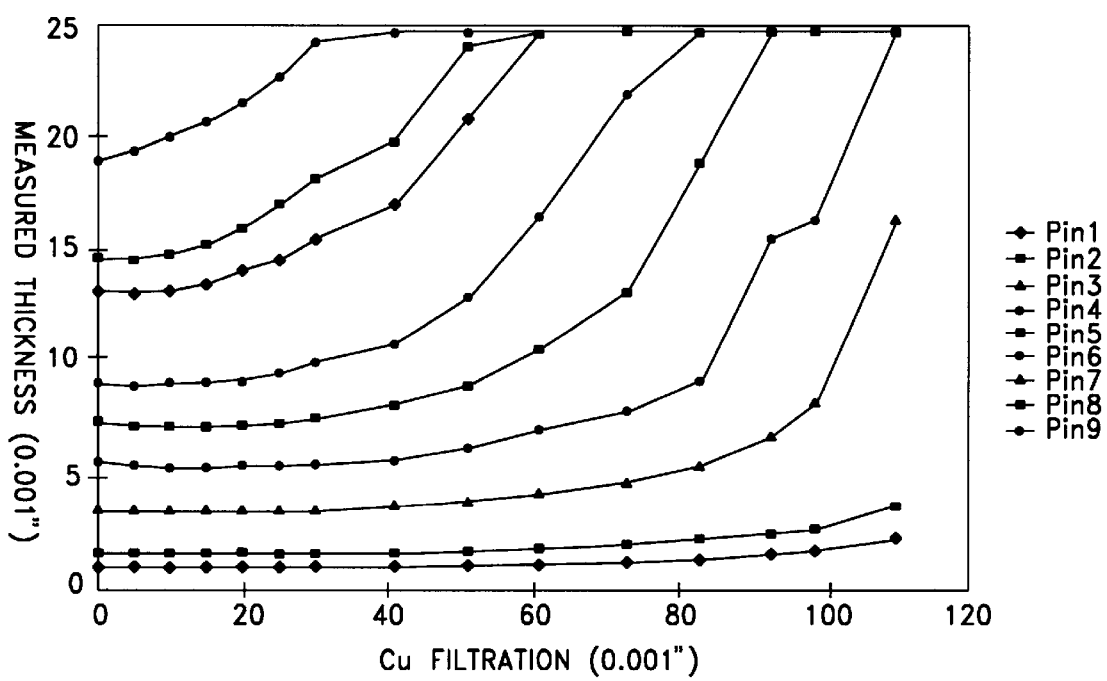
FIG. 10A shows the results of solder thickness vs. background determined by applying a linear shading correction to the data illustrated in FIG. 9.
Figure 10B:
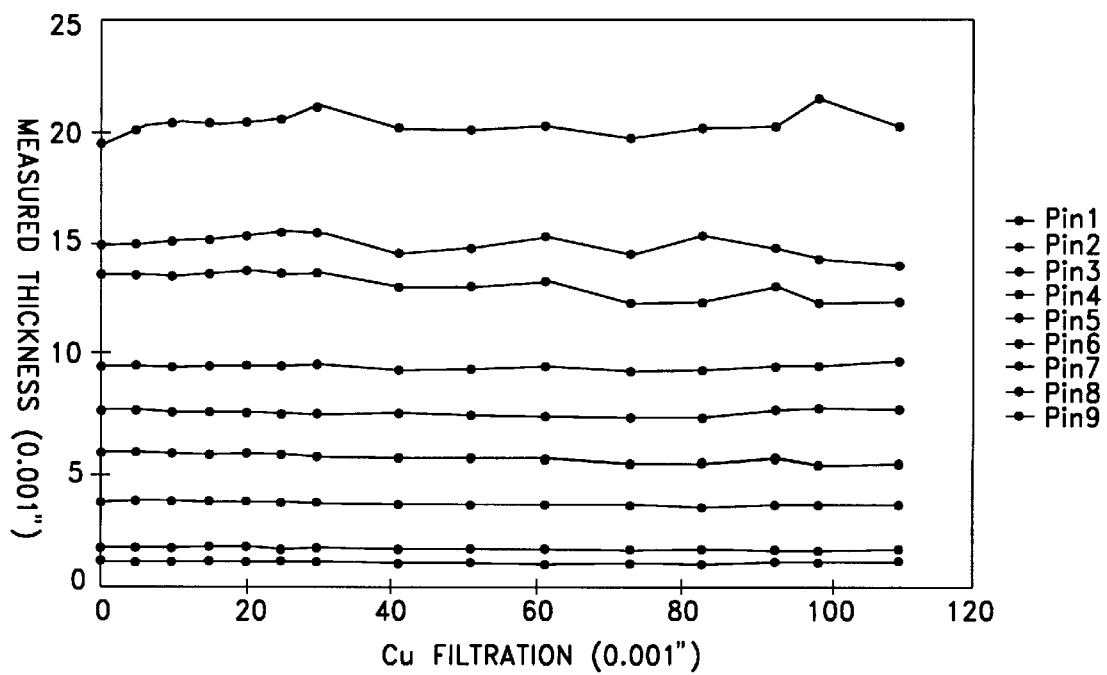
FIG. 10B shows the results of solder thickness vs. background determined by applying a non-linear shading correction to the data illustrated in FIG. 9.

A comparison of the linear shading correction technique to the non-linear shading correction technique is illustrated in FIGS. 10A and 10B. FIG. 10A shows calculated solder thickness vs. copper background thickness for the 9 sets of calibration data, where the solder thicknesses were calculated with the linear shading correction technique. It is evident from FIG. 10A that the linear shading correction technique results in overestimating the solder thicknesses as the background copper thicknesses increase. FIG. 10B shows calculated solder thickness vs. copper background thickness for the 9 sets of calibration data, where the solder thicknesses were calculated with the non-linear shading correction technique (hyperbolic fits). The non-linear shading correction technique clearly results in more accurate determinations of solder thicknesses, especially as the background copper thicknesses increase.

TWO DIMENSIONAL (2-D) SOLDER THICKNESS DETERMINATION

It is often advantageous, in terms of calculation speeds, etc., to represent solder calibration information in terms of a surface or look up table (LUT) defined in terms of Background (x or BG) vs. Delta Gray (y or ΔG) vs. Solder Thickness (t). Such a surface or LUT may be generated by the following procedure:
1) Measure a number of calibration points, e.g., the 9 sets of data shown in FIG. 9; and
2) Construct a DeLaunay Triangulation of the x vs. y (i.e., BG vs. ΔG) plane and use linear or polynomial interpolation to fill in the thickness values on a regular grid of x vs. y (i.e., BG vs. ΔG) which results in a 2D lookup table (LUT) of solder thickness (t) as a function of Background (x or BG) vs. Delta Gray (y or ΔG).

However, this approach may result in several problems, including: 1) a coordinate singularity at $x = BG = BG_{MAX} = x_0$; 2) artifactual "ripples", extrema, ridges, etc. in the surface; and 3) no physically meaningful surface outside the samples region unless extrapolation is employed, in which case it may be highly inaccurate and unreliable.

Many of these problems may be overcome by the following procedure. Recalling the physics of X-ray attenuation in connection with a 2 component assembly as described FIG. 5, a foreground intensity (i.e., image gray level) $y_f$ is described by the general functional form:

$$y_f = y_0 - \int \alpha(E) e^{-\beta(E) t_1} e^{-\gamma(E) t_2} dE \tag{22}$$

or its discrete approximation:

$$y_f = y_0 - \Sigma_i \alpha_i e^{-\beta_i t_1} e^{-\gamma_i t_2} \tag{23}$$

where $t_1$ and $t_2$ are the thicknesses of the first material and the second material, respectively. In the general functional form: 1) the X-ray source energy spectrum is distributed as a function of energy with weightings determined by the parameter α(E); and 2) β(E) and γ(E) are the X-ray attenuation coefficients for the first and second materials, respectively. In the discrete approximation: 1) the total X-ray source energy spectrum is split up into some number of bands i, where the total source intensity is distributed among the bands as a functions of X-ray source energy and detector sensitivity with weightings for each band i determined by the parameter $\alpha_i$; and 2) $\beta_i$ and $\gamma_i$ are the effective linear attenuation coefficients for X-rays in band i for the first and second materials, respectively. The following discussion is in terms of the discrete approximation, however, one skilled in the art will understand that a similar process also applies to the general functional form. A background intensity (i.e., image gray level) $y_b$ ($t_2$=0) is described in the discrete approximation form by:

$$y_b = y_0 - \Sigma_i \alpha_i e^{-\beta_i t_1} \tag{24}$$

Delta gray, the difference between the foreground and the background, is given by:

$$\Delta G = y_f - y_b = \Sigma_i \alpha_i e^{-\beta_i t_1} - \Sigma_i \alpha_i e^{-\beta_i t_1} e^{-\gamma_i t_2} \tag{25}$$

Using measured values of foreground ($y_f$) and background ($y_b$), or equivalently, $\Delta G$, for a series of calibration standards with known values of $t_1$ and/or $t_2$ for each calibration standard, the background measurements are used to do a least squares fit to $y_0$, $\alpha_i$ and $\beta_i$ for i=1 to n, where n, the number of bands is specified in advance, according to equation (24). Using these fitted values of $y_0$, $\alpha_i$ and $\beta_i$ for i=1 to n, the foreground measurements are used to do a least squares fit to the $\gamma_i$'s for i=1 to n, according to equation (23).

Figure 11A:
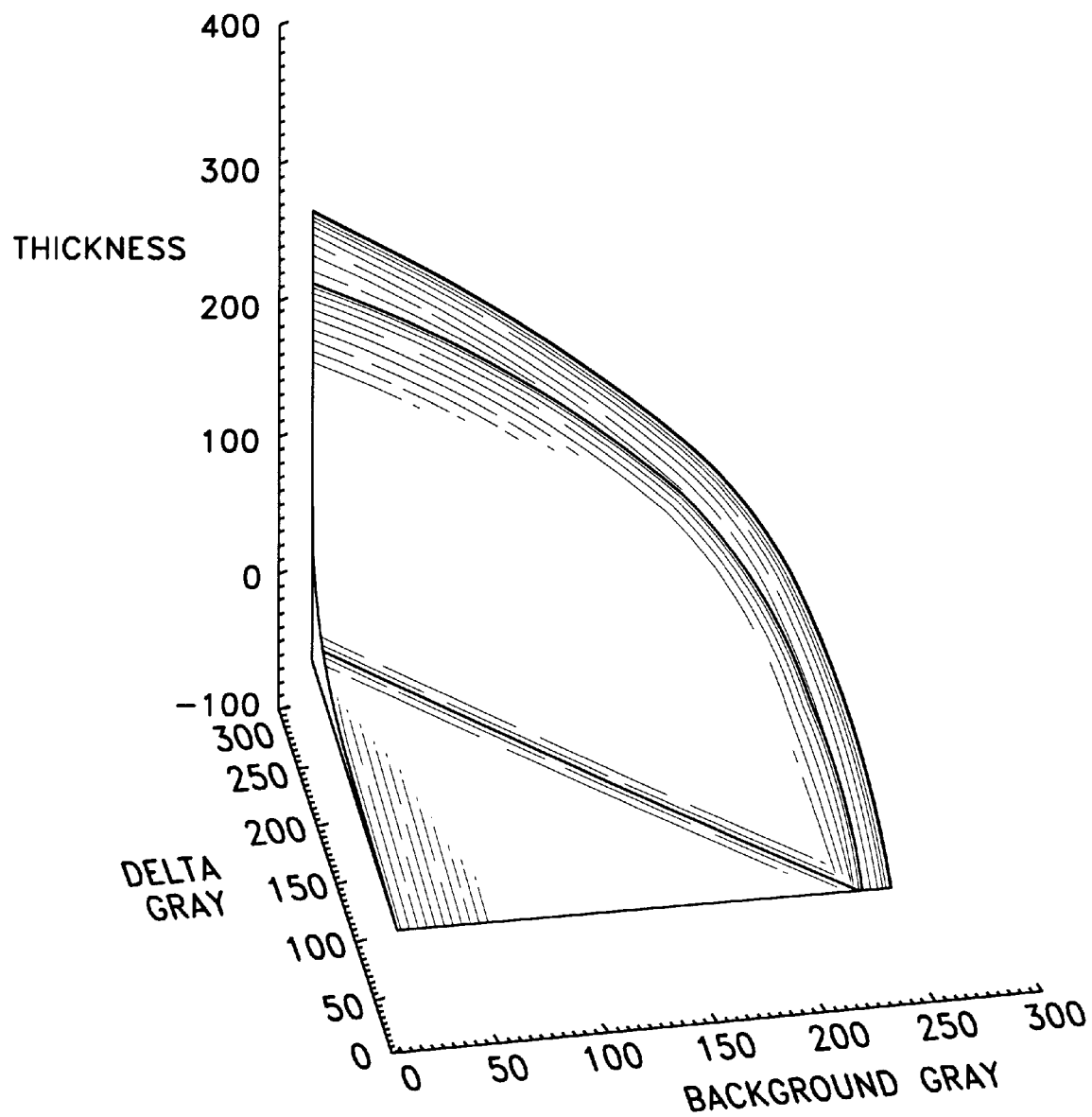
FIG. 11A shows an example of a Background (BG) vs. Delta Gray ($\Delta G$) vs. Solder Thickness (t) surface (generated from the calibration data illustrated in FIG. 9) in accordance with the present invention.

An internally consistent approximation to the actual Background (BG) vs. Delta Gray ($\Delta G$) vs. Solder Thickness (t) surface or look up table (LUT), which is free of ripples and supports consistent extrapolation, can be generated using these fitted values of the $y_0$, $\alpha_i$, $\beta_i$ and $\gamma_i$ parameters. Alternatively, it is noted that these parameters may also be obtained by simulation rather than regression, or by a combination of the two methods. For example, one could simulate the $\alpha_i$, $\beta_i$ and $\gamma_i$ parameters and fit the $y_0$ or fit $y_0$ and scale $\alpha_i$, $\beta_i$ and $\gamma_i$. One may also utilize the non-linear shading correction procedure described above to generate a surface or LUT which is consistent and free of ripples. FIG. 11A shows an example of such a Background (BG) vs. Delta Gray ($\Delta G$) vs. Solder Thickness (t) surface (generated from the calibration data illustrated in FIG. 9) in accordance with the above discussion.

Regardless of how the parameters $y_0$, $\alpha_i$, $\beta_i$ and $\gamma_i$ are obtained, an internally consistent look up table can be generated. For each background value desired in the look up table, equation (24) is solved for $t_1$. This can be done using Newton's Method or a simple Golden Section Search. Since it is known that there is a solution and the function is convex, a binary search is better than a Golden Section Search. Throughput is not critical since this is done only to construct the look up table. For each foreground value desired in the look up table, equation (23) is solved for $t_2$ using the previously determined value of $t_1$. Thus, in the 2D lookup table, the entry $t_1$ is placed in Row=$y_b$ at Col=$y_f$. Note that only half of a square array is needed in most cases. However, if it is desired to have the ability to read out values of $t_2$, then the values of $t_2$ can be stored in the other half of the array.

Figure 11B:
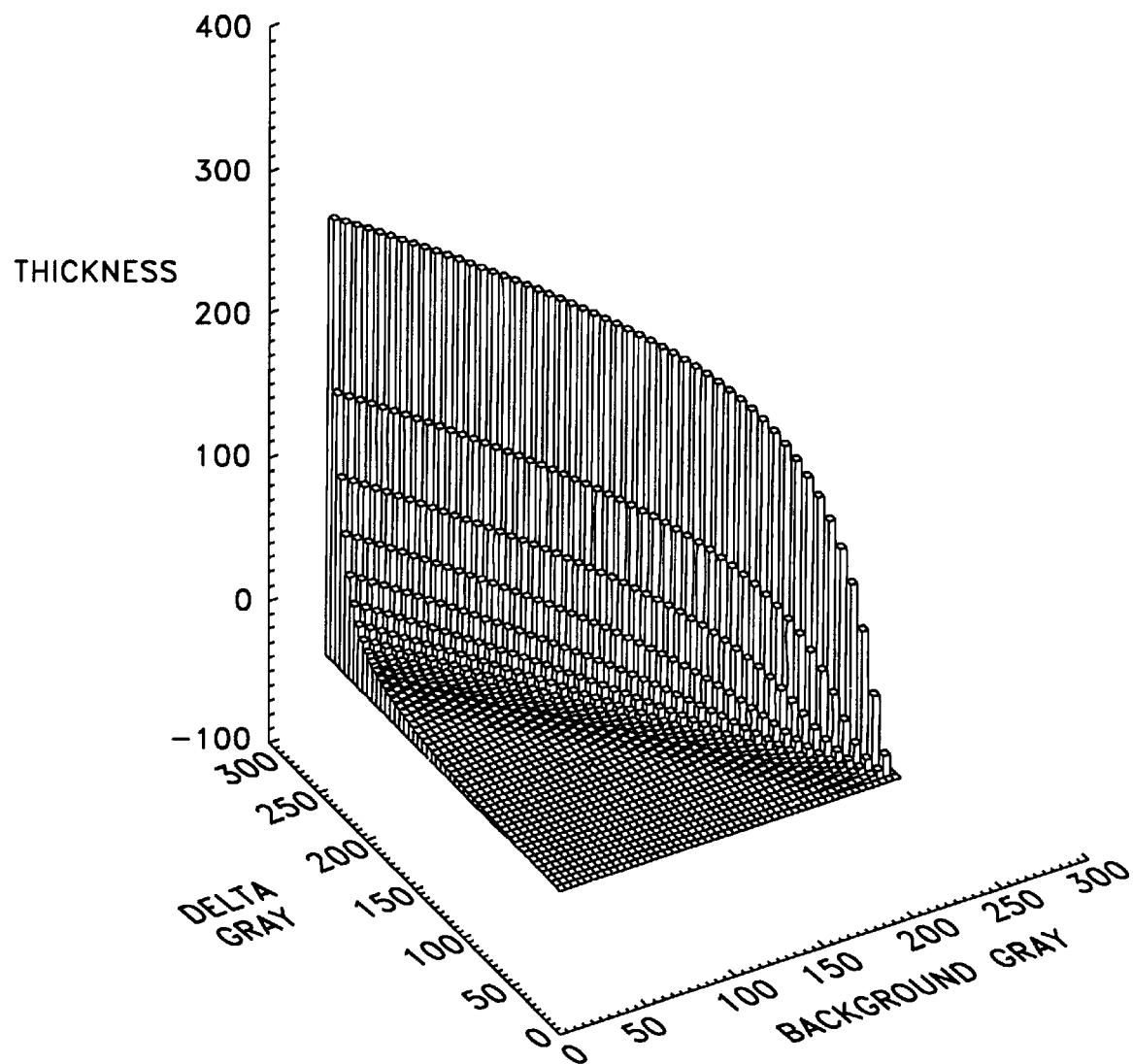
FIG. 11B shows a graphical representation of a Look Up Table (LUT) for Background (BG) vs. Delta Gray ($\Delta G$) vs. Solder Thickness (t) (generated from the calibration data illustrated in FIG. 9) in accordance with the present invention.
Figure 12:
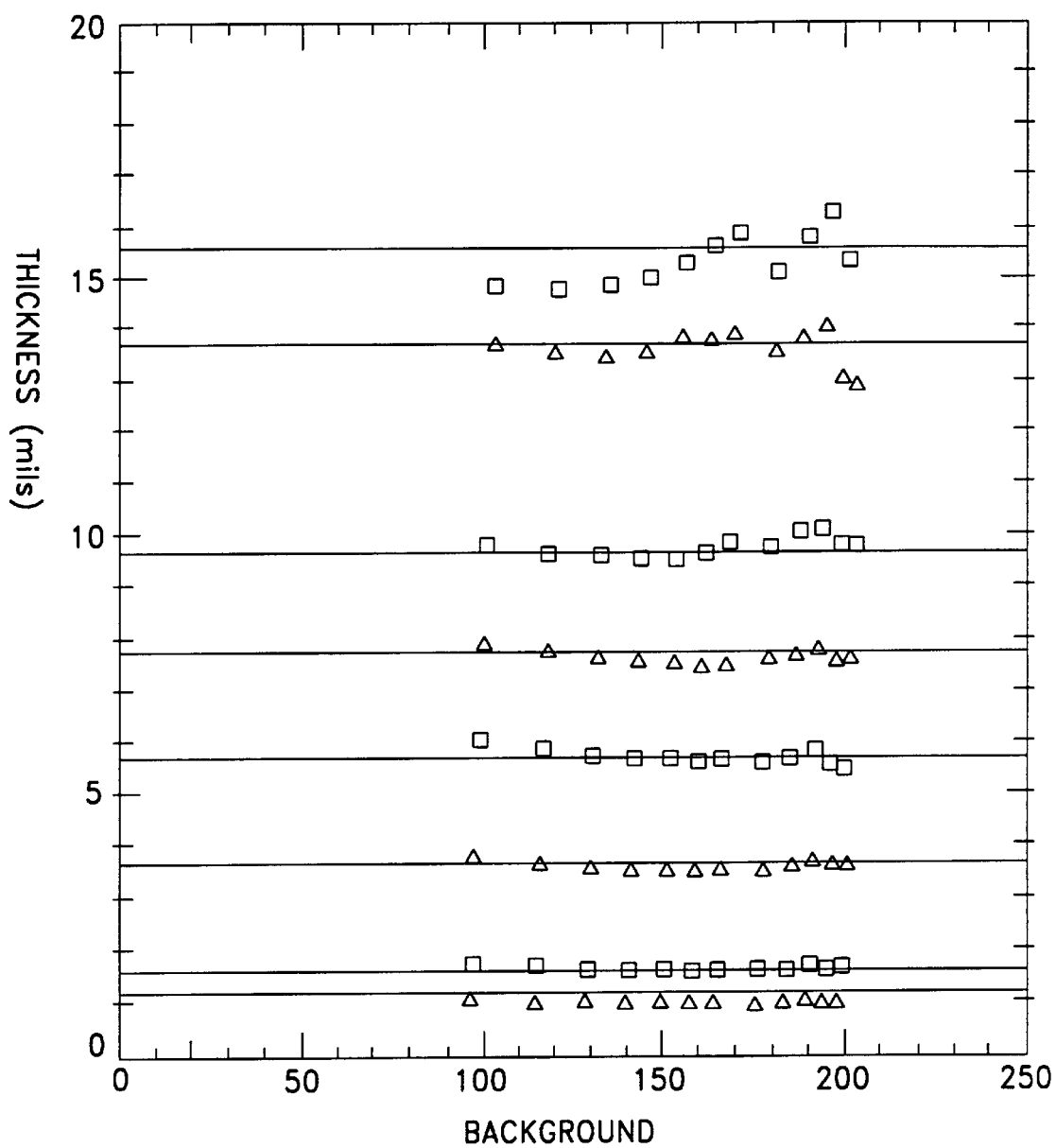
FIG. 12 shows the results of solder thickness vs. background determined from a lookup table (generated from the calibration data illustrated in FIG. 9) in accordance with the present invention.

In operation, the look up table is used as follows. Assume that the look up table is constructed using integer gray values from 0 to 255 for foreground and background entries. To look up the thickness t corresponding to a specific background/foreground pair, (BG,FG), let:

$R_1 = \lfloor BG \rfloor$ $R_2 = \lceil BG \rceil$ $C_1 = \lfloor FG \rfloor$ $C_2 = \lceil FG \rceil$ where $\lfloor x \rfloor$ is equal to the greatest integer $\leq x$ and $\lceil x \rceil$ is equal to the smallest integer $\geq x$. The thickness corresponding to (BG,FG) can then be estimated by bilinear interpolation. For example, let:

$t_a = t[R_2, C_1]$ $t_b = t[R_2, C_2]$ $t_c = t[R_1, C_2]$ $t_d = t[R_1, C_1]$ and $u = (BG - R_1)/(R_2 - R_1)$ $v = (FG)/(C_2 - C_1)$ Then, $t(BG, FG) \approx uvt_b + (1-u)vt_c + (1-u)(1-v)t_d + u(1-v)t_a$ Other interpolation schemes may be used, including linear interpolation from the three nearest points, or higher order schemes. Also note that if either FG or BG is an integer, interpolation in that axis (row or column) may be skipped for greater throughput. If both FG and BG are integers, the corresponding thickness value may be looked up directly. FIG. 11B shows a graphical representation of a Look Up Table (LUT) for Background (BG) vs. Delta Gray ($\Delta G$) vs. Solder Thickness (t) (generated from the calibration data illustrated in FIG. 9) in accordance with the present invention. Shown in FIG. 12 are the results of solder thickness vs. background determined from a lookup table (generated from the calibration data illustrated in FIG. 9) in accordance with the above discussion.

The above embodiments of the present invention have been described in terms of generating a procedure, look up table or surface from which an unknown thickness which corresponds to known values of the background and delta gray may be determined. However, these techniques are invertible in that: 1) an unknown background value which corresponds to known values of the thickness and delta gray may also be determined; and 2) an unknown delta gray value which corresponds to known values of the thickness and background may also be determined.

SINGLE MATERIAL CALIBRATION

The previous descriptions have been in the context of a first material, for example solder, shaded by a second material, for example, G10 circuit board material. However, the invention also applies to a single material calibration, for example, solder shaded by solder. An example where this might occur is the inspection of the solder joints on a BGA component, where a significant portion of the background surrounding the images of specific solder joints is due to the solder comprising surrounding solder joints.

The procedure for this situation is similar to the procedures described above. First, the gray levels of a plurality of different, known thicknesses of solder $T_i$ mounted on an appropriate substrate are measured. A curve of the following form (or its equivalent):

$$y_{F=y0} - \Sigma_i \alpha_i e^{-\beta_i T_i} \quad (26)$$

is fit to the measured values of known thicknesses. In many cases, two energy bands are probably sufficient, however, additional energy bands can be used if required to obtain the desired accuracy. The fit may be accomplished by fitting all of $y_0$, $\alpha_i$ and $\beta_i$. However, if $y_0$ is known, only the remaining parameters need to be fit. Thus, given a solder background measurement B and a solder foreground measurement F, equation (26) may be inverted to find the two corresponding thicknesses $T_F$ and $T_B$. The thickness of interest, i.e., the thickness of the solder joint, is then given by $T_{F-TB}$.

As before, this procedure may also be implemented with simulated calibration data. Simulation factors may include: a) spectral characteristics of the X-ray source; and/or b) angular distribution of X-rays produced by the X-ray source; and/or c) stopping power and spectral sensitivity of the X-ray detector; and/or d) X-ray attenuation properties of the absorbing materials as functions of X-ray energy/wavelength. Additionally, the procedure may be implemented with the construction of a look up table.

SUMMARY, RAMIFICATIONS AND SCOPE

Accordingly, the reader will see that the present invention solves many of the specific problems encountered when inspecting solder connections on circuited board assemblies. Particularly important is that it improves the accuracy of solder thickness measurements derived from X-ray images of solder connections.

Furthermore, the present invention has the additional advantages in that it provides a single, globally consistent calibration for any chosen material in the presence of varying amounts of shading by a second material;

it is fast in terms of its computational requirements;

it is compact in terms of its storage requirements;

it is more accurate than previous methods;

it is numerically invertible such that in a three parameter system, any one of the parameters may be determined from known values of the other two parameters;

it may be made traceable to known standards criteria, for example, the National Institute of Standards & Technology (NIST) or similar standards agencies. This feature permits process engineers to relate thicknesses measured by the X-ray system to physical joint dimensions. Traceability can be achieved by constructing the calibration standard out of materials of known purity, and by measuring thicknesses of the calibration standard using instruments which themselves have a traceable calibration;

it is portable, in the sense that measurement of the same joint on multiple systems will return similar or identical thicknesses. Portability requires that the calibration compensates for the physically significant sources of variation between systems; and it supports multiple calibrations. With the advent of lead-free solders, the joint and background compositions can vary from board to board, or even within a board. As a result, it is desirable to be able to store multiple calibrations simultaneously, and to permit the user to select the appropriate calibration on a pin, component, or board level.

Although the description above contains many specificities, these should not be construed as limiting the scope of the invention but as merely providing illustrations of some of the presently preferred embodiments of this invention. For example, alternative techniques for fitting the calibration data may be used; alternative techniques may be used to determine fitting parameters; alternative interpolation techniques may be used; alternative techniques may be used to acquire the cross sectional images; shadowgraph X-ray images (non-cross sectional) images may be employed; simulation may employed to determine some of the fitting parameters; the invention may be applied to assemblies having more than two layers; etc.

It is to be understood that the methods of the present invention may be implemented in a variety of ways by one skilled the art, however, implementation with the computer or specially dedicated image processor is preferred. A typical computer used for such analysis includes one or more processors, one or more memories and various input and output devices including but not limited to monitors, disk drives, printers and keyboards. Additionally, it is to be understood that the term "image" is not limited to formats which may be viewed visually, but may also include digital or analog representations which may be acquired, stored and analyzed by the computer.

Thus, the scope of the invention should be determined by the appended claims and their legal equivalents, rather than by the foregoing description and examples given. All changes which come within the meaning and range of equivalency of the claims are to be embraced within their scope.

I claim:

1. A method for calibrating an X-ray imaging system for quantitatively determining the thickness of a first absorbing material in the presence of a second absorbing material where an incident X-ray beam having an incident X-ray beam intensity is transmitted through the first and second absorbing materials, said method comprising the steps of:

providing a calibration standard having: a) multiple combinations of a first known thickness of the first absorbing material (denoted by $t_{M1,1}$) in combination with three thicknesses of the second absorbing material (denoted by $t_{M2,1}$, $t_{M2,2}$ and $t_{M2,3}$); and b) multiple combinations of a second known thickness of the first absorbing material (denoted by $t_{M1,2}$) in combination with three thicknesses of the second absorbing material (denoted by $t_{M2,4}$, $t_{M2,5}$ and $t_{M2,6}$);

determining the values of first, second and third foreground parameters (denoted by $F_1$, $F_2$ and $F_3$) wherein: a) the first foreground parameter $F_1$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,1}$; b) the second foreground parameter $F_2$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,2}$; and c) the third foreground parameter $F_3$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,3}$;

determining the values of first, second and third background parameters (denoted by $B_1$, $B_2$ and $B_3$)

wherein: a) the first background parameter $B_1$ is representative of a transmitted X-ray beam intensity corresponding to a portion of the incident X-ray beam intensity which is transmitted through only the second absorbing material having the thickness $t_{M2,1}$; b) the second background parameter $B_2$ is representative of a transmitted X-ray beam intensity corresponding to a portion of the incident X-ray beam intensity which is transmitted through only the second absorbing material having the thickness $t_{M2,2}$; and c) the third background parameter $B_3$ is representative of a transmitted X-ray beam intensity corresponding to a portion of the incident X-ray beam intensity which is transmitted through only the second absorbing material having the thickness $t_{M2,3}$;

determining the values of fourth, fifth and sixth foreground parameters (denoted by $F_4$, $F_5$ and $F_6$) wherein: a) the fourth foreground parameter $F_4$ is representative of a transmitted X-ray beam intensity corresponding to a portion of the incident X-ray beam intensity which is transmitted through the first absorbing material having the thickness $t_{M1,2}$ in combination with the second absorbing material having the thickness $t_{M2,4}$; b) the fifth foreground parameter $F_5$ is representative of a transmitted X-ray beam intensity corresponding to a portion of the incident X-ray beam intensity which is transmitted through the first absorbing material having the thickness $t_{M1,2}$ in combination with the second absorbing material having the thickness $t_{M2,5}$; and c) the sixth foreground parameter $F_6$ is representative of a transmitted X-ray beam intensity corresponding to a portion of the incident X-ray beam intensity which is transmitted through the first absorbing material having the thickness $t_{M1,2}$ in combination with the second absorbing material having the thickness $t_{M2,6}$;

determining the values of fourth, fifth and sixth background parameters (denoted by $B_4$, $B_5$ and $B_6$) wherein: a) the fourth background parameter $B_4$ is representative of a transmitted X-ray beam intensity corresponding to a portion of the incident X-ray beam intensity which is transmitted through only the second absorbing material having the thickness $t_{M2,4}$; b) the fifth background parameter $B_5$ is representative of a transmitted X-ray beam intensity corresponding to a portion of the incident X-ray beam intensity which is transmitted through only the second absorbing material having the thickness $t_{M2,5}$; and c) the sixth background parameter $B_6$ is representative of a transmitted X-ray beam intensity corresponding to a portion of the incident X-ray beam intensity which is transmitted through only the second absorbing material having the thickness $t_{M2,6}$; and determining a first functional form of a non-linear function, $y_1(x)$, which describes the value of the foreground minus the background ($y_1 = F - B$) as a function of background ($x = B$) such that the non-linear functional form: a) approximates the following values of foreground minus background: ($F_1-B_1$), ($F_2-B_2$), ($F_3-B_3$), ($F_4-B_4$), ($F_5-B_5$) and ($F_6-B_6$); b) supports extrapolation beyond the range of the values of foreground minus background {($F_1-B_1$), ($F_2-B_2$), ($F_3-B_3$), ($F_4-B_4$), ($F_5-B_5$), ($F_6-B_6$)} and/or foreground {$F_1, F_2, F_3, F_4, F_5, F_6$} and/or background {$B_1, B_2, B_3, B_4, B_5, B_6$}; and c) incorporates one or more additional constraints determined by or approximating the physical behavior of the X-ray imaging system.

2. The method of claim 1 wherein the steps of determining the values of the foreground and background parameters further comprise the steps of:

illuminating the calibration standard with a beam of X-rays having the incident X-ray beam intensity, wherein the beam of X-rays is produced by an X-ray source; and measuring the values of the foreground and background parameters with an X-ray detector.

3. The method of claim 1 wherein the steps of determining the values of the foreground and background parameters further comprises the step of simulating the values of the foreground and background parameters using one or more of the following simulation factors: a) spectral characteristics of the X-ray source; and/or b) angular distribution of X-rays produced by the X-ray source; and/or c) stopping power and spectral sensitivity of the X-ray detector; and/or d) X-ray attenuation properties of the first and second absorbing materials as functions of X-ray energy/wavelength.

4. The method of claim 1 wherein the foreground parameters $F_i$ are described by a functional form, $y_F$:

$$y_F = y_0 - \int \alpha(E) e^{-\beta(E) t_1} e^{-\gamma(E) t_2} dE$$

or its discrete approximation:

$$y_F = y_0 - \Sigma_i \alpha_i e^{-\beta_i t_1} e^{-\gamma_i t_2}$$

where $t_1$ and $t_2$ are the thicknesses of the first absorbing material and the second absorbing material, respectively; $y_0$ is a fitting constant; and, in the general functional form: a) the X-ray source energy spectrum is distributed as a function of energy with weightings determined by the parameter $\alpha(E)$; and b) $\beta(E)$ and $\gamma(E)$ are the X-ray attenuation coefficients for the first and second absorbing materials, respectively, and in the discrete approximation: c) the total X-ray source energy spectrum is split up into some number of bands i, where the total source intensity is distributed among the bands as a functions of X-ray source energy and detector sensitivity with weightings for each band i determined by the parameter $\alpha_i$; and d) $\beta_i$ and $\gamma_i$ are the effective linear attenuation coefficients for X-rays in band i for the first and second absorbing materials, respectively.

5. The method of claim 1 wherein the step of determining a first functional form of a smoothly varying non-linear function which expresses the value of the foreground minus the background ($y_1 = F - B$) as a function of background ($x = B$) comprises the step of selecting a function of the form:

$$y_1 = \sqrt{(x-a)^2 + b^2} + c$$

where x corresponds to the background $B_i$, $y_1$ corresponds to the difference between the foreground and background ($F_i - B_i$), and a, b and c are fitting constants.

6. The method of claim 1 further comprising the steps of:

selecting a reference background level ($x = B_R$);

determining the values of foreground minus background ($F_{Ri} - B_{Ri}$) at the reference background level ($B_R$) for multiple known thicknesses of the calibration standard using the smoothly varying non-linear function $y_1$ which expresses the value of the foreground minus the background ($y_1 = F - B$) as a function of background ($x = B$); and determining a second functional form $y^2$ which expresses the values of foreground minus background ($F_{Ri} - B_{Ri}$) at the reference background level ($B_R$) for the multiple known thicknesses of the first absorbing material as a function of the thickness of the first absorbing material.

7. The method of claim 6 wherein the step of determining a second functional form $y^2$ further comprises the step of selecting a function which is a sum of exponentials of the form:

$$y_2(t) = p - \Sigma_i q_i e^{-r_i t}$$

where p, $q_i$ and $r_i$ are fitting constants.

8. The method of claim 6 further comprising the step of producing a lookup table for values of (background) vs. (foreground minus background) vs. (thickness) for one or both of the first and/or second absorbing materials.

9. The method of claim 8 further comprising the steps of:
   determining the value of a seventh foreground parameter (denoted by $F_7$) which is representative of a transmitted X-ray beam intensity corresponding to a portion of the incident X-ray beam intensity which is transmitted through the first absorbing material having an unknown thickness $t_{M1,7}$ in combination with the second absorbing material having an unknown thickness $t_{M2,7}$;
   determining the value of a seventh background parameter (denoted by $B_7$) which is representative of a transmitted X-ray beam intensity corresponding to a portion of the incident X-ray beam intensity which is transmitted through the second absorbing material having an unknown thickness $t_{M2,7}$; and
   using the lookup table and the values of $F_7$ and $B_7$ to determine one or both of the unknown thickness(es) of the first absorbing material ($t_{M1,7}$) and/or the second absorbing material ($t_{M2,7}$).

10. The method of claim 8 further comprising the step of interpolating between values in the lookup table.

11. The method of claim 10 where the step of interpolating further comprises the step of bilinear interpolation.

12. The method of claim 1 further comprising the step of selecting the thicknesses of the second absorbing material ($t_{M2,i}$) such that at least one of the values of the first, second and third background parameters (denoted by $B_1$, $B_2$ and $B_3$) is equal to at least one of the values of the fourth, fifth and sixth background parameters (denoted by $B_4$, $B_5$ and $B_6$).

13. The method of claim 1 further comprising the step of selecting the thicknesses of the second absorbing material ($t_{M2,i}$) such that at least two of the values of the first, second and third background parameters (denoted by $B_1$, $B_2$ and $B_3$) are equal and/or at least two of the values of the fourth, fifth and sixth background parameters (denoted by $B_4$, $B_5$ and $B_6$) are equal.

14. A method for measuring the thickness of a first material in the presence of a second material comprising the steps of:
   providing a calibration standard having: a) multiple combinations of a first known thickness of the first material in combination with a range of thicknesses of the second material; and b) multiple combinations of a second known thickness of the first material in combination with a range of thicknesses of the second material;
   exposing the calibration standard to a source of transmissive energy having an incident intensity;
   detecting the intensity of the transmissive energy which passes through the calibration standard, said detecting step further comprising the step of:
      acquiring multiple pairs of image data which are representative of a portion of the transmissive energy which is measured after transmission through the first and second materials, where a foreground value (F) in each pair of image data corresponds to a portion of the incident intensity which is transmitted through the known thickness of the first material in combination with one of the multiple thicknesses of the second material, and a background value (B) in each pair of transmitted intensities corresponds to a portion of the incident intensity which is transmitted through only the corresponding thickness of the second material which was in combination with the first material when the foreground value (F) was acquired;
   determining fitting constants a,b and c for each member of a family of hyperbolic curves which describe delta gray values ($y_1 = \Delta G = F - B$) as a function of background values (B), where each curve in the family represents delta gray values for a fixed known thickness of the first material in combination with a range of thicknesses of the second material, each of the hyperbolic curves having the general form of:

$$y_1 = \sqrt{(x-a)^2 + b^2} + c$$

where x corresponds to the background values (x=B); $y_1$ corresponds to the delta gray values ($y_1 = \Delta G = F - B$) for a fixed known thickness of the first material in combination with the range of thicknesses of the second material; and a, b and c are the fitting constants, wherein the fitting constants are determined such that each hyperbolic curve in the family has the same x-axis intercept ($BG_{MAX}$,0) and each hyperbolic curve in the family has a minimum value at the same value of x (x=a);
   determining for each known thickness of the first material, a delta gray level at a reference background level, i.e., $y_1(x=B_R)$, from the hyperbolic curve defined by the multiple pairs of image data for the respective known thickness of the first material; and
   determining fitting constants for a second functional form ($y_2$) which describes the delta gray level values at the reference background level, as a function of the known thicknesses (t) of the first material, where the functional form is:

$$y_2(t) = BG_{MAX} - \beta e^{-k_1 t} - (BG_{MAX} - \beta) e^{-k_2 t}$$

where fitting constants $\beta$, $k_1$ and $k_2$ are determined by fits to the known thicknesses of the first material and corresponding delta gray levels at the reference background level derived from the hyperbolic curves which describe the delta gray values ($y_1$) as a function of the background values (B).

15. A method for measuring the thickness of a first material in the presence of a second material comprising the steps of:
   providing a calibration standard having: a) multiple combinations of a first known thickness ($t_{M1,1}$) of the first material in combination with a range of thicknesses ($t_{M2,a}$, $t_{M2,b}$, ..., $t_{M2,n1}$) of the second material; and b) multiple combinations of a second known thickness ($t_{M1,2}$) of the first material in combination with a range of thicknesses ($t_{M2,n1+1}$, $t_{M2,n1+2}$, ..., $t_{M2,n1+n2}$) of the second material;
   exposing the calibration standard to a source of transmissive energy having an incident intensity;
   detecting the intensity of the transmissive energy which passes through the calibration standard and determining therefrom image data which are representative of a portion of the transmissive energy which is measured after transmission through the first and second materials, said detecting step further comprising the step of:
      acquiring multiple pairs of image data, where each pair includes a foreground value and a background value, for each known thickness of the first material ($t_{M1,1}$, $t_{M1,2}$) in combination with multiple thicknesses ($t_{M2,}$ $a$, $t_{M2,b}$, etc.) of the second material; where the foreground value ($y_f$) in each pair of image data corresponds to a portion of the incident intensity which is measured after transmission through the known thickness of the first material in combination with one of the multiple thicknesses of the second material, and the background value ($y_b$) in each pair of image data corresponds to a portion of the incident intensity which is measured after transmission through the corresponding thickness of the second material which was in combination with the first material when the foreground value ($y_F$) was acquired;

determining fitting constants $y_0$, $\alpha_i$ and $\beta_1$ from the calibration standard background values for a functional form which approximates the measured background values ($y_b$) as a function of the thickness, wherein the functional form is:

$$y_b = y_0 - \Sigma_i \alpha_i e^{-\beta_i t_{M2}}$$

determining fitting constants $y_i$, using the previously determined fitting constants $y_0$, $\alpha_i$ and $\beta_i$ from the calibration standard background values, for a functional form which approximates the measured foreground values ($y_f$) as a function of the thickness, wherein the functional form is:

$$y_f = y_0 - \Sigma_i \alpha_i e^{-\beta_i t_{M2}} e^{-\gamma_i t_{M1}}$$

where $t_{M1}$ and $t_{M2}$ are the thicknesses of the first material and the second material, respectively; and generating a Background ($y_b$) vs. Delta Gray ($\Delta G = y_f - y_b$) vs. First Material Thickness ($t_{M1}$) surface using the fitted values for $y_0$, $\alpha_i$ $\gamma_i$ and $\beta_i$.

16. The method of claim 15 wherein the step of acquiring multiple pairs of image data comprises the step of simulating the intensities of the transmissive energy which passes through the calibration standard using one or more of the following simulation factors: a) spectral characteristics of the source of transmissive energy; and/or b) angular distribution of the source of transmissive energy; and/or c) stopping power and spectral sensitivity of a transmissive energy detector; and/or d) transmissive energy attenuation properties of the absorbing material as a function of energy/wavelength of the source of transmissive energy.

17. The method of claim 15 further comprising the steps of:

measuring foreground and background values for a combination of the first and second materials having unknown thicknesses; and locating on the Background ($y_b$) vs. Delta Gray ($\Delta G = y_f - y_b$) vs. First Material Thickness ($t_{M1}$) surface, background and Delta Gray image data values corresponding to the measured background and foreground values to determine at least one of the corresponding first and/or second material thicknesses.

18. The method of claim 15 further comprising the step of generating a Background ($y_b$) vs. Delta Gray ($\Delta G = y_f - y_b$) vs. First Material Thickness ($t_{M1}$) and/or Second Material Thickness ($t_{M2}$) look up table using the fitted values for $y_0$, $\alpha_i$ $\gamma_i$ and $\beta_i$.

19. The method of claim 18 further comprising the steps of:

measuring foreground and background values for a combination of the first and second materials having unknown thicknesses; and locating on the Background ($y_b$) vs. Delta Gray ($\Delta G = y_f - y_b$) vs. First Material Thickness ($t_{M1}$) look up table, Background and Delta Gray intensity values corresponding to the measured background and foreground values to determine at least one of the corresponding first and/or second material thicknesses.

20. The method of claim 19 further comprising the step of interpolating between values in the lookup table.

21. A method for calibrating an X-ray imaging system for quantitatively determining the thickness of a first absorbing material in the presence of a second absorbing material where an incident X-ray beam having an incident X-ray beam intensity is transmitted through the first and second absorbing materials, said method comprising the steps of:

providing a calibration standard for characterizing the imaging system wherein the calibration standard includes a first known thickness of the first absorbing material (denoted by $t_{M1,1}$) in combination with two different thicknesses of the second absorbing material (denoted by $t_{M2,1}$ and $t_{M2,2}$);

determining values of first and second foreground parameters (denoted by $F_1$ and $F_2$) wherein: a) the first foreground parameter $F_1$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,1}$; and b) the second foreground parameter $F_2$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,2}$;

determining values of first and second background parameters (denoted by $B_1$ and $B_2$) wherein: a) the first background parameter $B_1$ is representative of a transmitted X-ray beam intensity corresponding to a portion of the incident X-ray beam intensity which is transmitted through only the second absorbing material having the thickness $t_{M2,1}$; and b) the second background parameter $B_2$ is representative of a transmitted X-ray beam intensity corresponding to a portion of the incident X-ray beam intensity which is transmitted through only the second absorbing material having the thickness $t_{M2,2}$;

determining a first non-linear functional form, $y_1(x)$, which describes values of foreground ($y_1 = F$) as functions of the background ($x = B$) such that the first non-linear functional form: a) approximates the previously determined values of the first and second foreground parameters ($F_1$ and $F_2$) in terms of the previously determined values of the first and second background parameters ($B_1$ and $B_2$); b) incorporates one or more additional constraints determined by or approximating the physical behavior of the X-ray imaging system; and c) provides means to extrapolate a third foreground parameter ($F_3$) at a corresponding third background parameter ($B_3$) to a reference background value ($x = B_R$), thereby determining a reference foreground value ($y_1 = F_R$) at the reference background value ($x = B_R$); and determining a second non-linear functional form, $y_2(x)$, which describes reference foreground values ($y_2 = F_{Ri}$) as a function of corresponding first absorbing material thicknesses ($x = t_{M1,i}$) such that the second non-linear functional form: a) approximates a reference foreground value ($y_2 = F_{R1}$) of the calibration standard first known thickness of the first absorbing material ($t_{M1,1}$)

at the reference background value ($x=B_R$); and b) incorporates one or more additional constraints determined by or approximating the physical behavior of the X-ray imaging system.

22. The method of claim 21 wherein the step of determining a first non-linear functional form, $y_1(x)$, further comprises the step of selecting hyperbolic functions as one of the additional constraints having characteristics determined by or approximating the physical behavior of the X-ray imaging system.

23. The method of claim 21 wherein the step of determining a second non-linear functional form, $y_2(x)$, further comprises the step of inverting, either numerically or analytically, the second non-linear functional form to obtain a first material thickness ($t_{M1,K}$) corresponding to a given reference foreground value ($y_2=F_{RK}$).

24. The method of claim 21 wherein the step of determining a second non-linear functional form, $y_2(x)$, further comprises the step of selecting a sum of exponential functions as one of the additional constraints having characteristics determined by or approximating the physical behavior of the X-ray imaging system.

25. The method of claim 21 wherein the steps of determining the values of the foreground and background parameters further comprise the step of simulating the values of the foreground and background parameters using one or more of the following simulation factors: a) spectral characteristics of an X-ray source; and/or b) angular distribution of X-rays produced by the X-ray source; and/or c) stopping power and spectral sensitivity of an X-ray detector; and/or d) X-ray attenuation properties of the first and second absorbing materials as functions of X-ray energy/wavelength.

26. A method for calibrating an X-ray imaging system for quantitatively determining the thickness of a first absorbing material in the presence of a second absorbing material where an incident X-ray beam having an incident X-ray beam intensity is transmitted through the first and second absorbing materials, said method comprising the steps of:

providing a calibration standard for characterizing the imaging system wherein the calibration standard includes a first known thickness of the first absorbing material (denoted by $t_{M1,1}$) in combination with two different thicknesses of the second absorbing material (denoted by $t_{M2,1}$ and $t_{M2,2}$);

determining values of first and second foreground parameters (denoted by $F_1$ and $F_2$) wherein: a) the first foreground parameter $F_1$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,1}$; and b) the second foreground parameter $F_2$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,2}$;

determining values of first and second background parameters (denoted by $B_1$ and $B_2$) wherein: a) the first background parameter $B_1$ is representative of a transmitted X-ray beam intensity corresponding to a portion of the incident X-ray beam intensity which is transmitted through only the second absorbing material having the thickness $t_{M2,1}$; and b) the second background parameter $B_2$ is representative of a transmitted X-ray beam intensity corresponding to a portion of the incident X-ray beam intensity which is transmitted through only the second absorbing material having the thickness $t_{M2,2}$; and determining a functional form of a non-linear function, $y(x_1,x_2)$, which describes the value of the thickness of the first material ($y=t_{M1}$) as a function of the foreground and background (e.g., $x_1=F$, $x_2=B$) such that the non-linear functional form: a) approximates a set of calibration data points $\{(t_{M1,i}, F_i, B_i)\}$ containing the previously determined first material thicknesses ($t_{M1,i}$), foreground parameters ($F_i$) and background parameters ($B_i$); b) incorporates one or more additional constraints determined by or approximating the physical behavior of the X-ray imaging system; and c) provides means to extrapolate beyond the range of the calibration standard foreground and background parameters.

27. The method of claim 26 wherein the step of determining a functional form of the non-linear function, $y(x_1, x_2)$, further comprises the step of selecting a sum of the product of two exponentials to represent the foreground parameters and a sum of single exponentials to represent the background parameters as the additional constraints having characteristics determined by or approximating the physical behavior of the X-ray imaging system.

28. The method of claim 26 wherein the step of determining a functional form of the non-linear function, $y(x_1, x_2)$, further comprises the step of inverting, either numerically or analytically, the non-linear functional form such that any one of y, $x_1$ or $x_2$ may be expressed as a function of the remaining two variables.

29. The method of claim 26 wherein the steps of determining the values of the foreground and background parameters further comprise the step of simulating the values of the foreground and background parameters using one or more of the following simulation factors: a) spectral characteristics of an X-ray source; and/or b) angular distribution of X-rays produced by the X-ray source; and/or c) stopping power and spectral sensitivity of an X-ray detector; and/or d) X-ray attenuation properties of the first and second absorbing materials as functions of X-ray energy/wavelength.

30. A method for calibrating an X-ray imaging system for quantitatively determining the thickness of a first absorbing material in the presence of a second absorbing material where an incident X-ray beam having an incident X-ray beam intensity is transmitted through the first and second absorbing materials, said method comprising the steps of:

providing a calibration standard for characterizing the imaging system wherein the calibration standard includes first and second known thicknesses of the first absorbing material (denoted by $t_{M1,1}$ and $t_{M1,2}$) in combination with a thickness of the second absorbing material (denoted by $t_{M2,1}$ and $t_{M2,2}$);

determining values of first and second foreground parameters (denoted by $F_1$ and $F_2$) wherein: a) the first foreground parameter $F_1$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,1}$; and b) the second foreground parameter $F_2$ is representative of a transmitted X-ray beam intensity corresponding to a portion of the incident X-ray beam intensity which is transmitted through the first absorbing material having the thickness $t_{M1,2}$ in combination with the second absorbing material having the thickness $t_{M2,2}$;

determining values of first and second background parameters (denoted by $B_1$ and $B_2$) wherein: a) the first background parameter $B_1$ is representative of a transmitted X-ray beam intensity corresponding to a portion of the incident X-ray beam intensity which is transmitted through only the second absorbing material having the thickness $t_{M2,1}$; and b) the second background parameter $B_2$ is representative of a transmitted X-ray beam intensity corresponding to a portion of the incident X-ray beam intensity which is transmitted through only the second absorbing material having the thickness $t_{M2,2}$;

determining a first non-linear functional form, $y_1(x)$, which describes values of foreground ($y_1=F$) as functions of the background ($x=B$) such that the first non-linear functional form: a) approximates the previously determined values of the first and second foreground parameters ($F_1$ and $F_2$) in terms of the previously determined values of the first and second background parameters ($B_1$ and $B_2$); b) incorporates one or more additional constraints determined by or approximating the physical behavior of the X-ray imaging system; and c) provides means to extrapolate a third foreground parameter ($F_3$) at a corresponding third background parameter ($B_3$) to a reference background value ($x=B_R$), thereby determining a reference foreground value ($y_1=F_R$) at the reference background value ($x=B_R$); and determining a second non-linear functional form, $y_2(x)$, which describes reference foreground values ($y_2=F_{Ri}$) as a function of corresponding first absorbing material thicknesses ($x=t_{M1,i}$) such that the second non-linear functional form: a) approximates a first reference foreground value ($y_2=F_{R1}$) of the calibration standard first known thickness of the first absorbing material ($t_{M1,1}$) at the reference background value ($x=B_R$) and a second reference foreground value ($y_2=F_{R2}$) of the calibration standard second known thickness of the first absorbing material ($t_{M1,2}$) at the reference background value ($x=B_R$); and b) incorporates one or more additional constraints determined by or approximating the physical behavior of the X-ray imaging system.

31. The method of claim 30 wherein the step of providing a calibration standard further comprises the step of selecting the second absorbing material such that the thickness $t_{M2,1}$ equals the thickness $t_{M2,2}$.

32. The method of claim 30 wherein the step of determining a first non-linear functional form, $y_1(x)$, further comprises the step of selecting hyperbolic functions as one of the additional constraints having characteristics determined by or approximating the physical behavior of the X-ray imaging system.

33. The method of claim 30 wherein the step of determining a second non-linear functional form, $y_2(x)$, further comprises the step of inverting, either numerically or analytically, the second non-linear functional form to obtain a first material thickness ($t_{M1,K}$) corresponding to a given reference foreground value ($y_2=F_{RK}$).

34. The method of claim 30 wherein the step of determining a second non-linear functional form, $y_2(x)$, further comprises the step of selecting a sum of exponential functions as one of the additional constraints having characteristics determined by or approximating the physical behavior of the X-ray imaging system.

35. The method of claim 30 wherein the steps of determining the values of the foreground and background parameters further comprise the step of simulating the values of the foreground and background parameters using one or more of the following simulation factors: a) spectral characteristics of an X-ray source; and/or b) angular distribution of X-rays produced by the X-ray source; and/or c) stopping power and spectral sensitivity of an X-ray detector; and/or d) X-ray attenuation properties of the first and second absorbing materials as functions of X-ray energy/wavelength.

36. A method for calibrating an X-ray imaging system for quantitatively determining the thickness of a first absorbing material in the presence of a second absorbing material where an incident X-ray beam having an incident X-ray beam intensity is transmitted through the first and second absorbing materials, said method comprising the steps of:

providing a calibration standard for characterizing the imaging system wherein the calibration standard includes first and second known thicknesses of the first absorbing material (denoted by $t_{M1,1}$ and $t_{M1,2}$) in combination with a thickness of the second absorbing material (denoted by $t_{M2,1}$ and $t_{M2,2}$);

determining values of first and second foreground parameters (denoted by $F_1$ and $F_2$) wherein: a) the first foreground parameter $F_1$ is representative of a transmitted X-ray beam intensity corresponding to a portion of the incident X-ray beam intensity which is transmitted through the first absorbing material having the thickness $t_{M1,1}$ in combination with the second absorbing material having the thickness $t_{M2,1}$; and b) the second foreground parameter $F_2$ is representative of a transmitted X-ray beam intensity corresponding to a portion of the incident X-ray beam intensity which is transmitted through the first absorbing material having the thickness $t_{M1,2}$ in combination with the second absorbing material having the thickness $t_{M2,2}$;

determining values of first and second background parameters (denoted by $B_1$ and $B_2$) wherein: a) the first background parameter $B_1$ is representative of a transmitted X-ray beam intensity corresponding to a portion of the incident X-ray beam intensity which is transmitted through only the second absorbing material having the thickness $t_{M2,1}$; and b) the second background parameter $B_2$ is representative of a transmitted X-ray beam intensity corresponding to a portion of the incident X-ray beam intensity which is transmitted through only the second absorbing material having the thickness $t_{M2,2}$; and determining a functional form of a non-linear function, $y(x_1,x_2)$, which describes the values of the thickness of the first material ($y=t_{M1}$) as a function of the foreground and background (e.g., $x_1=F$, $x_2=B$) such that the non-linear functional form: a) approximates a set of calibration data points $\{(t_{M1,i},F_i,B_i)\}$ containing the previously determined first material thicknesses ($t_{M1,i}$), foreground parameters ($F_i$) and background parameters ($B_i$); b) incorporates one or more additional constraints determined by or approximating the physical behavior of the X-ray imaging system; and c) provides means to extrapolate beyond the range of the calibration standard foreground and background parameters.

37. The method of claim 36 wherein the step of providing a calibration standard further comprises the step of selecting the second absorbing material such that the thickness $t_{M2,1}$ equals the thickness $t_{M2,2}$.

38. The method of claim 36 wherein the step of determining a functional form of the non-linear function, $y(x_1, x_2)$, further comprises the step of selecting a sum of the product of two exponentials to represent the foreground parameters and a sum of single exponentials to represent the background parameters as the additional constraints having characteristics determined by or approximating the physical behavior of the X-ray imaging system.

39. The method of claim 36 wherein the step of determining a functional form of the non-linear function, $y(x_1, x_2)$, further comprises the step of inverting, either numerically or analytically, the non-linear functional form such that any one of y, $x_1$ or $x_2$ may be expressed as a function of the remaining two variables.

40. The method of claim 36 wherein the steps of determining the values of the foreground and background parameters further comprise the step of simulating the values of the foreground and background parameters using one or more of the following simulation factors: a) spectral characteristics of an X-ray source; and/or b) angular distribution of X-rays produced by the X-ray source; and/or c) stopping power and spectral sensitivity of an X-ray detector; and/or d) X-ray attenuation properties of the first and second absorbing materials as functions of X-ray energy/wavelength.

41. A method for calibrating an X-ray imaging system for quantitatively determining a first thickness, $T_x$, of an absorbing material in the presence of an additional, second thickness, $T_y$, of the absorbing material, where an incident X-ray beam having an incident X-ray beam intensity is transmitted through the absorbing material, said method comprising the steps of:

providing a calibration standard for characterizing the imaging system wherein the calibration standard provides two known thicknesses $T_1$ and $T_2$ of the absorbing material;

determining values $F_1$ and $F_2$ reflective of transmitted X-ray beam intensities corresponding to transmission through thicknesses $T_1$ and $T_2$ of the absorbing material, respectively;

determining a functional form of an invertible, non-linear function $y(x)$ which describes the variation of transmitted X-ray beam intensity as a function of thickness of the absorbing material;

determining values B and F reflective of transmitted X-ray beam intensities corresponding to transmission through the second thickness, $T_y$, of the absorbing material and through the combined thickness, $T_x+T_y$, of the absorbing material, respectively;

applying the previously determined functional form to determine $T_y$ and $T_x+T_y$ from the measured values of F and B; and determining the unknown first thickness, $T_x$, as the difference $(T_x+T_y)-T_y$.

42. The method of claim 41 wherein the step of determining a functional form which describes transmitted beam intensity as a function of thickness further comprises selecting a general functional form described by:

$$y = y_0 - \int \alpha(E) e^{-\beta(E)T} dE$$

or its discrete approximation:

$$y = y_0 - \Sigma_i \alpha_i e^{-\beta_i T}$$

where T is the thickness of the absorbing material, $y_0$ is a fitting constant; and, in the general functional form: a) the X-ray source energy spectrum is distributed as a function of energy with weightings determined by the parameter $\alpha(E)$; and b) $\beta(E)$ is the X-ray attenuation coefficient for the absorbing material, and in the discrete approximation: c) the total X-ray source energy spectrum is split up into some number of bands i, where the total source intensity is distributed among the bands as a functions of X-ray source energy and detector sensitivity with weightings for each band i determined by the parameter $\alpha_i$; and d) $\beta_i$ is the effective linear attenuation coefficient for X-rays in band i for the absorbing material.

43. The method of claim 41 wherein the step of determining the values $F_1$ and $F_2$ comprises the step of simulating the transmitted intensities using one or more of the following simulation factors: a) spectral characteristics of the incident X-ray beam; and/or b) angular distribution of X-rays comprising the incident X-ray beam; and/or c) stopping power and spectral sensitivity of an X-ray detector; and/or d) X-ray attenuation properties of the absorbing material as a function of X-ray energy/wavelength.

44. An apparatus for calibrating an X-ray imaging system for quantitatively determining the thickness of a first absorbing material in the presence of a second absorbing material where an incident X-ray beam having an incident X-ray beam intensity is transmitted through the first and second absorbing materials, said apparatus comprising:

a calibration standard for characterizing the imaging system wherein the calibration standard includes at least one known thickness $t_{M1,i}$ of the first absorbing material in combination with at least one thickness $t_{M2,i}$ of the second absorbing material;

means for determining a value of foreground and background parameters (denoted by F and B) wherein: a) the foreground parameter F is representative of a transmitted X-ray beam intensity corresponding to a portion of the incident X-ray beam intensity which is transmitted through the first absorbing material having thickness $t_{M1,1}$ in combination with the second absorbing material having a thickness $t_{M2,i}$; and b) the background parameter B is representative of a transmitted X-ray beam intensity corresponding to a portion of the incident X-ray beam intensity which is transmitted through only the second absorbing material having the thickness $t_{M2,i}$; and means for determining a non-linear functional form which describes values of the foreground and/or the background and/or the material thicknesses such that the non-linear functional form: a) is consistent with the previously determined foreground parameter (F), background parameter (B), and thickness values; b) incorporates one or more additional constraints determined by or approximating the physical behavior of the X-ray imaging system; and c) provides means to extrapolate the foreground and/or the background and/or the material thicknesses beyond the range of the calibration standard.

45. The apparatus of claim 44 wherein the means for determining a non-linear functional form further comprises:

means for determining a first non-linear functional form, $y_1(x)$, which describes values of foreground ($y_1=F$) as functions of the background (x=B) such that the first non-linear functional form: a) approximates the previously determined value of the foreground parameter (F) in terms of the previously determined value of the background parameter (B); b) incorporates one or more additional constraints determined by or approximating the physical behavior of the X-ray imaging system; and c) provides means to extrapolate a measured foreground parameter ($F_M$) corresponding to a first absorbing material having an unknown thickness $t_{M1,U}$ in combination with a second absorbing material having a thickness $t_{M2,U}$ to a reference background value ($x=B_R$), thereby determining a reference foreground value ($y_1=F_{R,U}$) at the reference background value ($x=B_R$); and means for determining a second non-linear functional form, $y_2(x)$, which describes reference foreground values ($y_2=F_{Ri}$) as a function of corresponding first absorbing material thicknesses ($x=t_{M1,i}$) such that the second non-linear functional form: a) approximates a reference foreground value ($y^2=F_{R1}$) of the calibration standard for the known thickness of the first absorbing material ($t_{M1,1}$) at the reference background value ($x=B_R$); and b) incorporates one or more additional constraints determined by or approximating the physical behavior of the X-ray imaging system.

46. The apparatus of claim 44 wherein the means for determining a non-linear functional form further comprises:

means for determining a functional form of a non-linear function, $y(x_1,x_2)$, which describes the values of the thickness of the first material ($y=t_{M1}$) as a function of the foreground and background (e.g., $x_1=F$, $x_2=B$) such that the non-linear functional form: a) approximates a set of calibration data points $\{(t_{M1,i},F_i,B_i)\}$ containing the previously determined first material thicknesses ($t_{M1,i}$), foreground parameters ($F_i$) and background parameters ($B_i$); b) incorporates one or more additional constraints determined by or approximating the physical behavior of the X-ray imaging system; and c) provides means to extrapolate beyond the range of the calibration standard foreground and background parameters.

47. A method for calibrating an X-ray imaging system for quantitatively determining the thickness of a first absorbing material in the presence of a second absorbing material where an incident X-ray beam having an incident X-ray beam intensity is transmitted through the first and second absorbing materials, said method comprising the steps of:

providing a calibration standard for characterizing the imaging system wherein the calibration standard includes at least one known thickness $t_{M1,i}$ of the first absorbing material in combination with at least one thickness $t_{M2,i}$ of the second absorbing material;

determining a value of foreground and background parameters (denoted by F and B) wherein: a) the foreground parameter F is representative of a transmitted X-ray beam intensity corresponding to a portion of the incident X-ray beam intensity which is transmitted through the first absorbing material having thickness $t_{M1,i}$ in combination with the second absorbing material having a thickness $t_{M2,i}$; and b) the background parameter B is representative of a transmitted X-ray beam intensity corresponding to a portion of the incident X-ray beam intensity which is transmitted through only the second absorbing material having the thickness $t_{M2,i}$; and determining a non-linear functional form which describes values of the foreground and/or the background and/or the material thicknesses such that the non-linear functional form: a) is consistent with the previously determined foreground parameter (F), background parameter (B), and thickness values; b) incorporates one or more additional constraints determined by or approximating the physical behavior of the X-ray imaging system; and c) provides means to extrapolate the foreground and/or the background and/or the material thicknesses beyond the range of the calibration standard.

48. The method of claim 47 wherein the step of determining a non-linear functional form further comprises the steps of:

determining a first non-linear functional form, $y_1(x)$, which describes values of foreground ($y_1=F$) as functions of the background ($x=B$) such that the first non-linear functional form: a) approximates the previously determined value of the foreground parameter (F) in terms of the previously determined value of the background parameter (B); b) incorporates one or more additional constraints determined by or approximating the physical behavior of the X-ray imaging system; and c) provides means to extrapolate a measured foreground parameter ($F_M$) corresponding to a first absorbing material having an unknown thickness $t_{M1,U}$ in combination with a second absorbing material having a thickness $t_{M2,U}$ to a reference background value ($x=B_R$), thereby determining a reference foreground value ($y_1=F_{R,U}$) at the reference background value ($x=B_R$); and determining a second non-linear functional form, $y_2(x)$, which describes reference foreground values ($y_2=F_{Ri}$) as a function of corresponding first absorbing material thicknesses ($x=t_{M1,i}$) such that the second non-linear functional form: a) approximates a reference foreground value ($y_2=F_{R1}$) of the calibration standard for the known thickness of the first absorbing material ($t_{M1,1}$) at the reference background value ($x=B_R$); and b) incorporates one or more additional constraints determined by or approximating the physical behavior of the X-ray imaging system.

49. The method of claim 47 wherein the steps of determining the values of the foreground and background parameters further comprises the step of simulating the values of the foreground and background parameters using one or more of the following simulation factors: a) spectral characteristics of the X-ray beam; and/or b) angular distribution of X-rays comprising the X-ray beam; and/or c) stopping power and spectral sensitivity of an X-ray detector; and/or d) X-ray attenuation properties of the first and second absorbing materials as functions of X-ray energy/wavelength.

50. The method of claim 47 wherein the foreground parameters $F_i$ are described by a general functional form, $y_F$:

$$y_F = y_0 - \int \alpha(E) e^{-\beta(E)t_1} e^{-\gamma(E)t_2} dE$$

or its discrete approximation:

$$y_F = y_0 - \Sigma_i \alpha_i e^{-\beta_i t_1} e^{-\gamma_i t_2}$$

where $t_1$ and $t_2$ are the thicknesses of the first absorbing material and the second absorbing material, respectively; $y_0$ is a fitting constant; and, in the general functional form: a) the X-ray beam energy spectrum is distributed as a function of energy with weightings determined by the parameter $\alpha(E)$; and b) $\beta(E)$ and $\gamma(E)$ are the X-ray attenuation coefficients for the first and second absorbing materials, respectively, and in the discrete approximation: c) the total X-ray beam energy spectrum is split up into some number of bands i, where the total source intensity is distributed among the bands as a functions of X-ray beam energy and detector sensitivity with weightings for each band i determined by the parameter $\alpha_i$; and d) $\beta_i$ and $\gamma_i$ are the effective linear attenuation coefficients for X-rays in band i for the first and second absorbing materials, respectively.

51. The method of claim 47 wherein the step of determining a non-linear functional form comprises the step of selecting a function of the form:

$$y_1 = \sqrt{(x-a)^2 + b^2} + c$$

where x corresponds to the background B, $y_1$ corresponds to the difference between the foreground and background (F−B), and a, b and c are fitting constants.

52. The method of claim 51 further comprising the steps of:

selecting a reference background level ($x=B_R$);

determining the values of foreground minus background ($F_{Ri}-B_{Ri}$) at the reference background level ($B_R$) for multiple known thicknesses of the calibration standard using the smoothly varying non-linear function $y_1$ which expresses the value of the foreground minus the background ($y_1=F-B$) as a function of background ($x=B$); and determining a second functional form $y_2$ which expresses the values of foreground minus background ($F_{Ri}-B_{Ri}$) at the reference background level ($B_R$) for the multiple known thicknesses of the first absorbing material as a function of the thickness of the first absorbing material.

53. The method of claim 52 wherein the step of determining a second functional form $y_2$ further comprises the step of selecting a function which is a sum of exponentials of the form:

$$y_2(t) = p - \Sigma_i q_i e^{-r_i t}$$

where $p$, $q_i$ and $r_i$ are fitting constants.

54. The method of claim 47 further comprising the step of producing a lookup table for values of (background) vs. (foreground minus background) vs. (thickness) for one or both of the first and/or second absorbing materials.

55. The method of claim 47 wherein the step of determining a non-linear functional form further comprises the step of:

determining a functional form of a non-linear function, $y(x_1,x_2)$, which describes the values of the thickness of the first material ($y=t_{M1}$) as a function of the foreground and background (e.g., $x_1=F$, $x_2=B$) such that the non-linear functional form: a) approximates a set of calibration data points $\{(t_{M1,i},F_i,B_i)\}$ containing the previously determined first material thicknesses ($t_{M1,i}$), foreground parameters ($F_i$) and background parameters ($B_i$); b) incorporates one or more additional constraints determined by or approximating the physical behavior of the X-ray imaging system; and c) provides means to extrapolate beyond the range of the calibration standard foreground and background parameters.

* * * * *